(12) United States Patent
Aldana et al.

(10) Patent No.: US 9,498,552 B2
(45) Date of Patent: Nov. 22, 2016

(54) COMPOSITIONS AND METHODS FOR ELIMINATING MICROBIAL GROWTH AND PREVENTING ODORS IN VEHICLE HVAC SYSTEMS AND PASSENGER CABIN AND TRUCK ENVIRONMENTS

(75) Inventors: Leonardo Aldana, Mississauga (CA); Andrew Stanislaw Chochol, Mississauga (CA);
(Continued)

(73) Assignee: CPS Products Canada Ltd., Niagara Falls, Ontario (CA)

( * ) Notice: Subject to any disclaimer, the term of this patent is extended or adjusted under 35 U.S.C. 154(b) by 406 days.

(21) Appl. No.: 12/106,002

(22) Filed: Apr. 18, 2008

(65) Prior Publication Data
US 2008/0283626 A1   Nov. 20, 2008

Related U.S. Application Data

(63) Continuation-in-part of application No. PCT/CA2007/001548, filed on Aug. 31, 2007.
(Continued)

(51) Int. Cl.
*B05B 1/08* (2006.01)
*A61L 2/22* (2006.01)
(Continued)

(52) U.S. Cl.
CPC .. *A61L 2/22* (2013.01); *A61L 9/14* (2013.01); *B60H 1/008* (2013.01);
(Continued)

(58) Field of Classification Search
CPC .............. B60H 1/00264; B60H 3/0092; B60H 1/008; B05B 17/0607
(Continued)

(56) References Cited

U.S. PATENT DOCUMENTS 1,018,569 A * 2/1912 Kelty .................... 137/527.8
2,956,582 A * 10/1960 Pranter .................. F16K 1/16
                                                137/512.1
(Continued)

FOREIGN PATENT DOCUMENTS

CN       1071764      5/1993
EP       1092446      4/2001
(Continued)

OTHER PUBLICATIONS

Wynn's Aircomatic Ultrasonic Heating, Ventilation and Air Condition (HVAC) Cleaning System Services written by Wynn Oil Company, published May 2002.
(Continued)

*Primary Examiner* — Jason Boeckmann
(74) *Attorney, Agent, or Firm* — K&L Gates LLP

(57) ABSTRACT

A mist-generating device that can be connected to a vehicle's Low Direct Current Voltage (LDCV) power supply is disclosed. The device can be used to treat mold, bacteria and clean or remove odors on exposed and hard-to-reach surfaces of the interior of a car. The device can include a unique filling system that can be used to prevent foreign materials from entering into the unit, including fluids or substances that would deteriorate the performance of the unit or the components of the device itself. The inside of the device can include an internal anti-foam and anti-splash structure designed to keep electronic components dry and reduce the foaming and turbulence of the fluid being misted. Further, the inside of the device in one embodiment is split into three adjacent areas, which govern efficient flow of air and atomized chemicals through the device.

58 Claims, 20 Drawing Sheets

(75) Inventors: Tony Ferraro, Mississauga (CA);
Kerwyn Prescod, Angus (CA); Ting On Wong, Oakville (CA); Sasan Raissi, North York (CA)

Related U.S. Application Data

(60) Provisional application No. 60/824,370, filed on Sep. 1, 2006.

(51) Int. Cl.
| | |
|---|---|
| *A61L 9/14* | (2006.01) |
| *B60H 1/00* | (2006.01) |
| *B60H 3/00* | (2006.01) |
| *B05B 17/06* | (2006.01) |

(52) U.S. Cl.
CPC ........ *B60H 1/00264* (2013.01); *B60H 3/0085* (2013.01); *B60H 3/0092* (2013.01); *B05B 17/0607* (2013.01)

(58) Field of Classification Search
USPC ....... 222/91; 239/102.2, 338, 345, 370, 463, 239/468, 469; 137/404, 199, 204
See application file for complete search history.

(56) References Cited

U.S. PATENT DOCUMENTS

| | | | | |
|---|---|---|---|---|
| 2,999,648 | A | * | 9/1961 | Wahlin et al. ................ 239/487 |
| 3,838,706 | A | * | 10/1974 | Klenk et al. ............... 137/527.8 |
| 4,031,171 | A | * | 6/1977 | Asao et al. ........................ 261/1 |
| 4,640,804 | A | * | 2/1987 | Mizoguchi ...................... 261/81 |
| 5,429,302 | A | * | 7/1995 | Abbott ....................... 239/102.2 |
| 5,624,608 | A | * | 4/1997 | Ching et al. .................... 261/30 |
| 5,657,926 | A | | 8/1997 | Toda |
| 6,244,576 | B1 | * | 6/2001 | Tsai .............................. 261/141 |
| 6,357,671 | B1 | | 3/2002 | Cewers |
| 6,883,724 | B2 | * | 4/2005 | Adiga et al. ............... 239/102.1 |
| 7,129,619 | B2 | | 10/2006 | Yang et al. |
| 7,721,729 | B2 | * | 5/2010 | Von Hollen ...... A61M 15/0085 128/200.14 |
| 2004/0255936 | A1 | * | 12/2004 | Urbanus .................. 128/200.23 |
| 2005/0011916 | A1 | * | 1/2005 | Battista et al. ................ 222/576 |
| 2007/0088245 | A1 | * | 4/2007 | Babaev .............. A61H 23/0245 604/22 |
| 2008/0223953 | A1 | * | 9/2008 | Tomono et al. ........... 239/102.2 |
| 2008/0245362 | A1 | * | 10/2008 | Moessis et al. ......... 128/200.16 |

FOREIGN PATENT DOCUMENTS

| | | | |
|---|---|---|---|
| FR | 2690510 | | 10/1993 |
| JP | 53091415 | A * | 8/1978 |
| WO | 2008/025168 | | 3/2008 |
| WO | 2008/025168 | A1 | 3/2008 |

OTHER PUBLICATIONS

Wynn's Aircomatic II Ultrasonic Heating, Ventilation and Air Condition (HVAC) Cleaning System Services written by Wynn Oil Company, published Sep. 2005.
Product Specification Sheet for Wynn's Aircomatic Ultrasonic Heating, Ventilation and Air Condition (HVAC) Cleaning System Services written by Wynn Oil Company, published May 2002.
Product Specification Sheet for Wynn's Aircomatic II Ultrasonic Heating, Ventilation and Air Condition (HVAC) Cleaning System Services written by Wynn Oil Company, published Sep. 2005.
Bernoulli's principle writen by http://en.wikipedia.org/wiki/Bernoulli's_equation (website), printed Apr. 10, 2008.
European Search Report for 07800572.5-2113/2056969 PCT/A2007/001548.
International Search Report for PCT/CA2009/00521.
Wynn's Aircomatic II Product Specification Sheet.
Boyle's law (http://en.wikipedia.org/wiki/Boyle's law) printed Jul. 13, 2009.
Bernoulli's principle (http://en.wikipedia.org/wiki/Bernouslli%27s principle).
Chinese Office Action issued on Sep. 27, 2012 for corresponding Chinese Patent Application No. 200780038556.8
Canadian Office Action dated Jul. 3, 2013 for corresponding Canadian Patent Application No. 2661747.
Chinese Office Action issued on May 2, 2013 for corresponding Chinese Patent Application No. 200780038556.8.
Chinese Office Action issued on Jan. 28, 2012 for corresponding Chinese Patent Application No. 200780038556.8.
Chinese Office Action issued on Dec. 5, 2012 for corresponding Chinese Patent Application No. 200980120985.9.
European Office Action issued on Mar. 19, 2012 for corresponding European Patent Application No. 07800572.5.
Chinese Office Action issued on Jul. 24, 2013 for corresponding Chinese Patent Application No. 200980120985.9.
Chinese Office Action issued on Mar. 11, 2014 for corresponding Chinese Patent Application No. 200980120985.9.
Canadian Office Action issued on Apri 24, 2014 for Application No. 2,661,747.
Office Action issued on May 1, 2015 for Canadian Patent Application No. 2,719,231 (4 pages).
European Search Report issued on Mar. 24, 2015 for Application No. 09733549.1 (11 pages).
Examiner Action issued on Jan. 18, 2016 for Canadian Patent Application No. 2,661,747.
Examiner Action issued on Mar. 29, 2016 for Canadian Patent Application No. 2,719,321.

* cited by examiner

COMPOSITIONS AND METHODS FOR ELIMINATING MICROBIAL GROWTH AND PREVENTING ODORS IN VEHICLE HVAC SYSTEMS AND PASSENGER CABIN AND TRUCK ENVIRONMENTS

PRIORITY CLAIM

This application is a continuation-in-part application of PCT Application No. PCT/CA2007/001548, filed on Aug. 31, 2007, entitled "Compositions and Methods for Eliminating and Preventing Vehicle Odors," which claimed priority to U.S. Provisional Application Ser. No. 60/824,370, filed on Sep. 1, 2006, entitled "Compositions and Methods for Eliminating and Preventing Vehicle Odors," the entire contents of which are hereby fully incorporated by reference.

BACKGROUND

Vehicles often accumulate odors inside their cabins during their lifetime of use. Such odors can be caused in a variety of ways and by a variety of sources. For example, objects left inside the vehicle, volatile organic compounds (VOCs) from the cabin interior materials, activities such as smoking and eating and the accumulation of dust and other pollutants suspended in the air can all contribute to the accumulation of odors. Eventually odors inside a vehicle become annoying and in some cases they may become a health risk if the source of odor involves bacteria, mold (fungi) or other microorganisms.

Besides the obvious surfaces that become contaminated with pollutants, like the seats, dashboards, carpets and other visible parts of the interior of a vehicle there are some hidden areas that create a perfect environment for pollutants, such as fungi, to accumulate and grow to a level where they can be noticed by smell even before they are visible. There are also many germs, bacteria and mold (fungi) that are present and are odorless.

One location for the growth and/or accumulation of hidden pollutants is in the interior of the air conditioning system. Typical air conditioning units include a chamber, where the refrigerant serpentine, also known as evaporator core, is embedded. Under normal operating conditions of a properly functioning air conditioning system, the serpentine condenses the moisture coming into the chamber due to the interaction between temperature, the existing dew point, and the relative humidity inside and outside the vehicle. In this process, the air entering the system contacts the cold interior parts of the system which retain and condense the humidity from the air. The cooler drier air comforts passengers once it exits the system, vents, and enters the vehicle cabin.

The condensation causes water to flow along the walls of the serpentine and the evaporator as well as the inside of the ventilation system. The accumulated water exits the chamber through a drain hole/hose designed specifically for this purpose. However, the surfaces inside the unit and ventilation system can remain humid for extended periods of time that vary from minutes to months depending on usage and climate conditions.

Year after year the air conditioning system is turned on and off and suspended dust, dirt, pollen, mold (fungi), bacteria and other polluting agents in the air enter the chamber passing into the evaporator chamber as the air conditioner blower draws air through the system both from the cabin and from the exterior of the vehicle through the air intake. Some of the particles from the polluted air adhere to the moist surfaces of the serpentine or other internal walls of the chamber as the air passes through the evaporator. In addition, some of the pollutants pass through the system and can become deposited over the interior surfaces of the cabin. The accumulated particles on the moist surfaces of the evaporator provide an environment in which micro-organisms can grow, particularly in the absence of UV light from the sun. The growth of microbial pollutants inside the evaporator further increases the amount of pollutants and odors that can enter the cabin in the airflow created by the blower. Automobile manufacturers have recognized a need for cleaning air conditioning systems for years. For example, U.S. Pat. No. 5,385,028 to General Motors discloses what is said to be a method of eliminating odor in a heat pump system of a vehicle that includes the steps of detecting removal of the vehicle passengers and ignition key after use of the cooling mode or air conditioning of the passenger compartment heat exchanger, operating the blower, reversing the flow of refrigerant in the heat pump to place the passenger compartment heat exchanger in heating mode to remove latent moisture. U.S. Pat. No. 5,259,813 to Mercedes discloses a method for deciding whether to recirculate air. The quality of the external air is determined by means of a pollutant sensor. The quality of the internal air is determined by calculation taking account of the air quantities introduced from outside into the internal space. A decision between air supply operation and air recirculation operation is then made on the basis of a comparison of the air qualities inside and outside. The pollutant sensor is preferably located in a casing whose internal space is accessible to gases through an opening which is preferably sealed by a gas-permeable membrane to eliminate odor. The proliferation of carbon air filters in new vehicles provides an indication of the consumers awareness of the air space in a vehicle and their desire for cleaner air. Even the US military has needs for air quality of cooled air as evidenced by U.S. Pat. No. 5,386,823.

Contaminants and odors can also originate from inside the passenger compartment and these also can circulate through the ventilation system and inside the evaporator when the air conditioner is operating. As an example, tobacco smoke originating from within the passenger compartment can cause odor in fabric headliners, upholstery and carpets all of which can be transported through the ventilation system and inside the evaporator. Further, any moisture accumulations in any part of the cabin can provide a place for mold and bacteria to grow. The mold can generate spores that can become suspended in the air inside the cabin. These spores can then re-circulate through the air conditioning system. Because of the moisture and temperature activity inside the evaporator and the lack of light, many of these contaminants and particles tend to accumulate inside the evaporator unit, creating layers of what appears to be "mud". When the air conditioning is turned on spores in the system can be blown out into the cabin which can actually create a health risk in certain individuals. At best, this situation creates an annoying bad-smelling odor every time the A/C and/or the heater are turned on.

Methods for removing or treating these mold, bacteria and odors inside the evaporator and ventilation system have been developed. One method is to spray a foaming aerosol solution through the evaporator drain hole. The foam then expands into foam inside the evaporator. However, the rapid expansion from an aerosol to a foam state prevents the foam from effectively reaching the upper recesses of the evaporator. In addition, the method is complicated by the need to either remove the evaporator or raise the vehicle on a lift in order to reach the drain hole, or drill a hole in the evaporator case to allow a straw type aerosol injector access. These are all labor intensive operations requiring a person to position the vehicle appropriately, position and hold the aerosol can while depressing the valve releasing its contents.

Another method involves spraying a non-foaming aerosol solution into the exterior-located air intake, while the blower motor is running. However, because the aerosol droplets of the spray are heavier than air, and significantly larger at about 40-100 microns in size. They do not travel effectively and far enough to reach the inside of the evaporator or the entire ventilation system. Neither of these solutions is designed to treat interior cabin surfaces for micro-organisms and contaminants and both are labor-intensive in that the operator must continuously depress the valve on the aerosol can in order to release it's contents. Airsept, Inc. provides one such product. Alternatively, electronics can be used to keep the evaporator dry. See e.g., U.S. Pat. Nos. 5,899,082 and 6,840,051.

Other methods for treating odor-causing contaminants involve generating a vapor out of a cleaning solution inside the passenger compartment. Spray devices for carrying out this process can be pointed into the intake(s) of the air conditioning re-circulating system of the vehicle while the air conditioning system is in operation. The vapor-saturated air then circulates through the evaporator and the ventilation system, the cleaning solution can condense on the inside walls of the evaporator and vents and can flow into the passenger compartment. As this happens, the cleaning solution comes into contact and interacts with contaminants, thus removing or reducing mold, bacteria and odors. Another factor for treating is the volume of solution put into a passenger cabin over a given time. There needs to be enough surface time for the effectiveness of any solution and time of getting the solution into the compartment in a minimum amount of time.

Several methods are known for vaporizing a cleaning solution. In one method a vapor is created by using an ultrasonic piezo-transducer. However, such devices have a number of drawbacks in the automobile cleaning environment such that they have not been used in the past. For example, existing devices require a high voltage alternating current (AC) to operate, which places limitations on the application of these devices, as they are dependent on this type of power being available in close proximity in order for a vehicle to be serviced with this device and method. AC-powered devices of this nature are limited to areas of a building or shop with access to AC electricity. Ultimately, the current required to produce a sufficient amount of vapor from such a device has led manufacturers away from making portable systems.

Several devices operated by high voltage alternating current are known. For example, Wynn's AIRCOMATIC® Ultrasonic Air Conditioning Cleaning System. Wynn's AIR-COMATIC II® Ultrasonic Heating, Ventilation & Air Conditioning Cleaning System, which uses ultrasonic technology but needs to be connected to high AC voltage. The VAPORTEK® Restorator uses electric heat, but no ultrasonic technology and is powered by either AC or low voltage direct current (LVDC) in different versions. The AIR-CLEAN-EVAPORATOR® which uses same technology as the VAPORTEK® Restorator, but is only powered by a high AC voltage version and the Wurth EVAPOclean®, which uses ultrasonic technology but requires high voltage AC power supply.

Each of these devices requires an electrical cable, or extension cord, that extends from an AC power source to the unit which is positioned inside a vehicle for use. The cable or cord transits through the vehicle's window or door. The vehicle window or door must be shut tight against the cord in order to minimize external air contaminants from entering the vehicle and not allowing the treatment to exit the vehicle. However, the thickness of the cable or cord leaves a gap to external air in the vehicle compartment which decreases the effectiveness of the service as a portion of the mist escapes through the gap. Moreover, the resulting pressure exerted from the window or door on the cable or cord can be sufficient to cut or strip insulation material and expose live wires that can lead to a short circuit and potentially a fire since these devices work with High AC Voltage. For these reasons such devices have not come into popular use.

For a piezoelectric transducer to operate properly, it is important that the liquid that is converted to vapor will not damage the device by corrosion, scaling or accumulation of residues. Since the device is meant to be used by a diverse group of people, there is the potential that different cleaning solutions may be used, either accidentally or deliberately, in the device. All of the known products allow for any type cleaning solution or chemical to be used, providing no control over what is used in the unit. This makes it highly likely that eventually the unit will be damaged by an unsuitable cleaning solution or be made unsafe to the occupants by someone using a commercially available cleaning solution like Windex, Febreeze, bleach or chlorine. The refill openings of known devices are even big enough to drop solids into the machine that will affect its performance. This is yet another reason why such devices are not widely used for cleaning automobile ventilation systems.

Some of the existing devices are configured in such a way that the turbulence, foam and/or splashing created by the piezoelectric transducers inside the "misting" chamber soaks some special mechanisms or components in the fluid, affecting their performance and durability of the device. Some devices have a level measuring system that signal the machine to stop when the fluid is low. The splashing and turbulence in these devices can in some instances create false signals stopping the device prematurely. In some cases the foaming and turbulence can also affect the amount of mist coming out of the device.

The vaporizing performance of a piezoelectric transducer is dependent on the amount of fluid over it and this is influenced by the angle of tilt of the device. Since existing devices don't have any way to orient the user on whether the equipment is really in an upright position, the performance of the equipment may be affected negatively without the knowledge of the user. For example, when the machine includes a level sensor and the machine is tilted a number of degrees from the horizontal, the machine may either work longer, which would damage the piezoelectric transducers if the level goes too low on one side; or the machine may stop its cycle earlier, which causes an insufficient amount of fluid use in the treatment.

The existing devices require close monitoring to ensure that treatments are finished and that machines are working properly. Most of the known devices display such information on their sides, which means that to monitor them in an automobile, the door of the vehicle must be opened and the technician must lean over and check the side of the device for that information.

For all of the above reasons known devices have not come into widespread use and new devices and methods for cleaning automobile ventilation systems are needed.

SUMMARY

Various embodiments of a vaporizing-generator are disclosed that are particularly useful for automotive odor treatment and removal. Various embodiments of the vapor generator can operate from a vehicle's direct current power supply, such as a 12 or 24 volt direct current electric power supply. Because the device operates from Low Voltage Direct Current (LVDC) it can be used in a wide variety of vehicles. The device can also be operated through special transformers or power supplies. Another advantage of this device is that it can be operated in virtually any location including such remote areas as parking lots, farms, trade shows, on-the-road demonstrations, and the like.

Additional features and advantages are described herein, and will be apparent from, the following Detailed Description and the figures.

BRIEF DESCRIPTION OF THE FIGURES

FIG. 19 provides a perspective view of another embodiment of the device 100, the device not having its external cover on.

DETAILED DESCRIPTION

Figure 1:
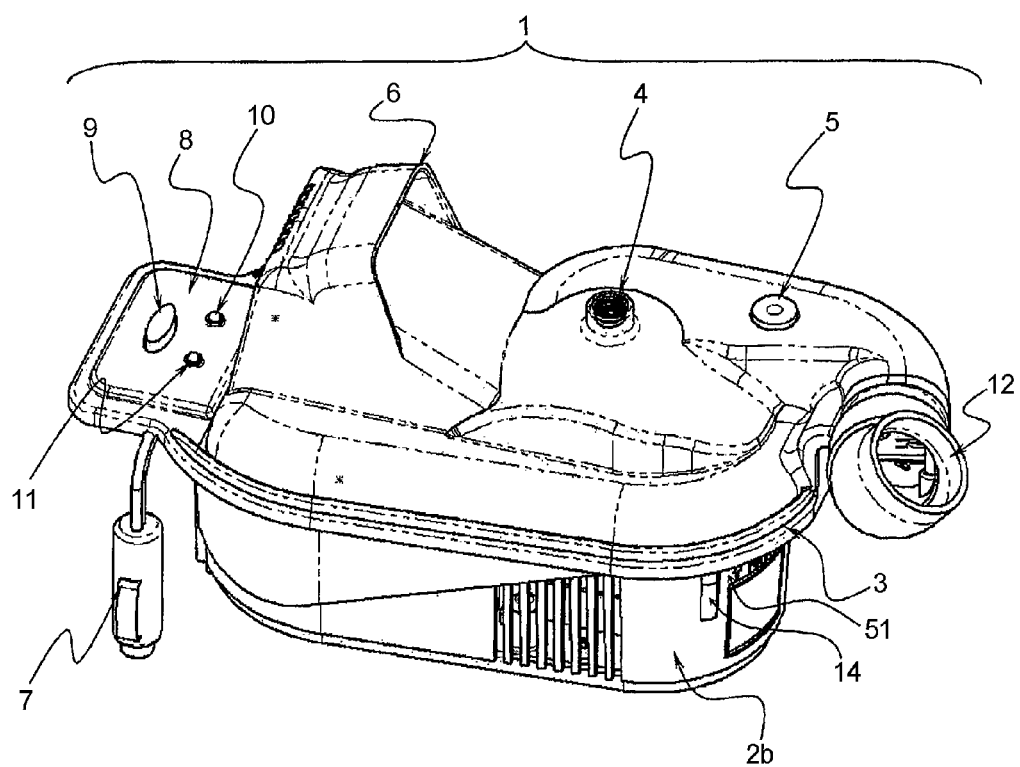
FIG. 1 provides an elevated view of an embodiment of the device 1.
Figure 2:
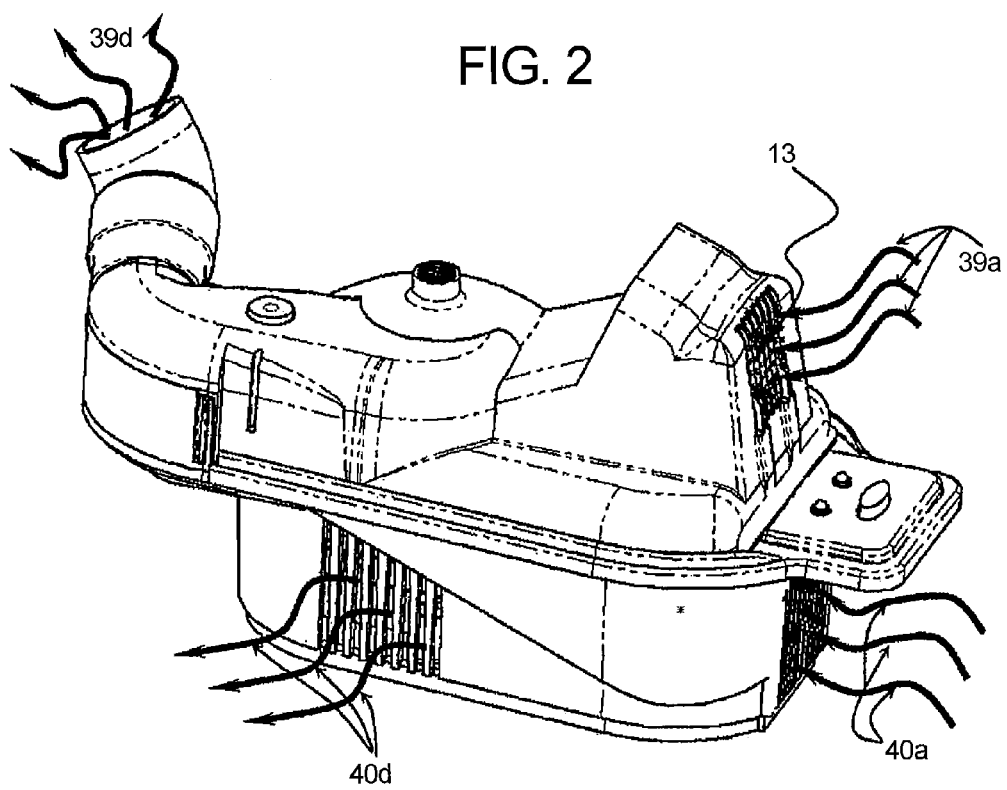
FIG. 2 provides an elevated view of an embodiment of the device and illustrates one pattern of external air flows.
Figure 3:
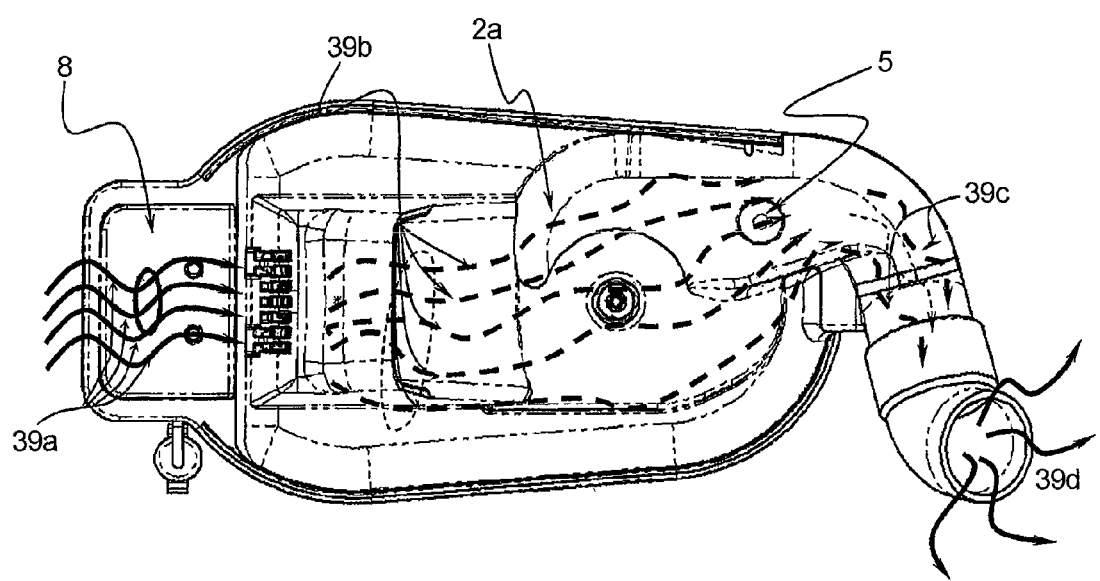
FIG. 3 provides a top view of an embodiment of the device and illustrates one pattern of air flow through the top of the device.
Figure 4:
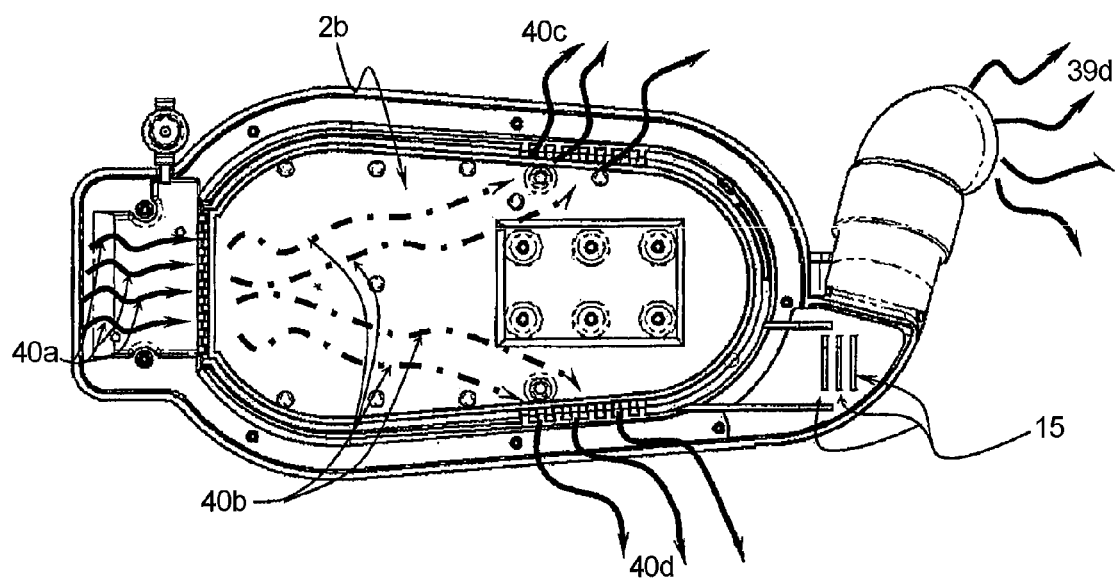
FIG. 4 provides a bottom view of an embodiment of the device and illustrates air flow through the bottom of the device.
Figure 5:
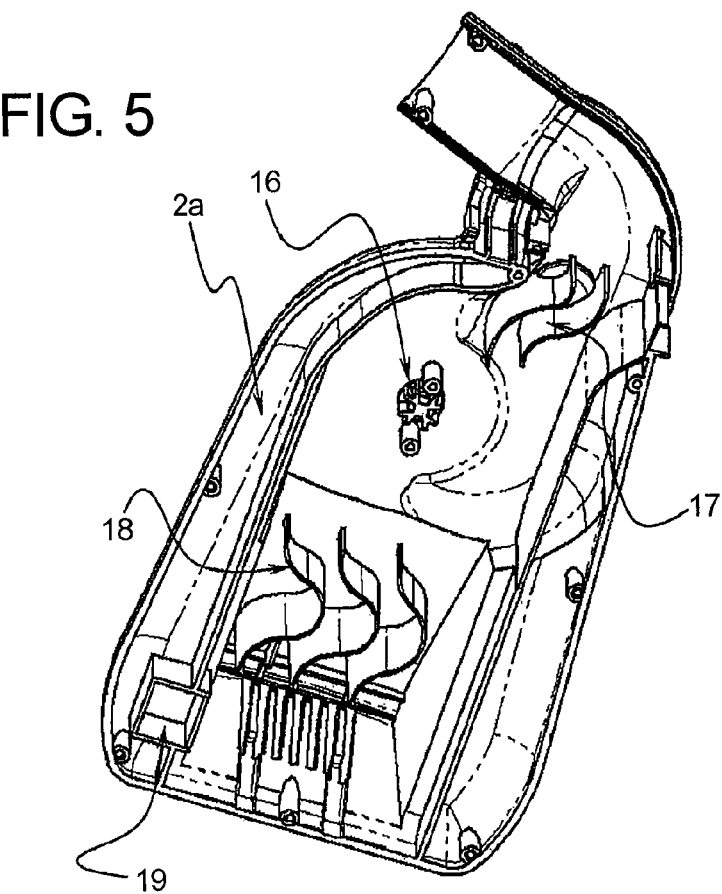
FIG. 5 provides a top view of an embodiment of the top cover 2a of the device 1 having splash guards 17 and 18.
Figure 6:
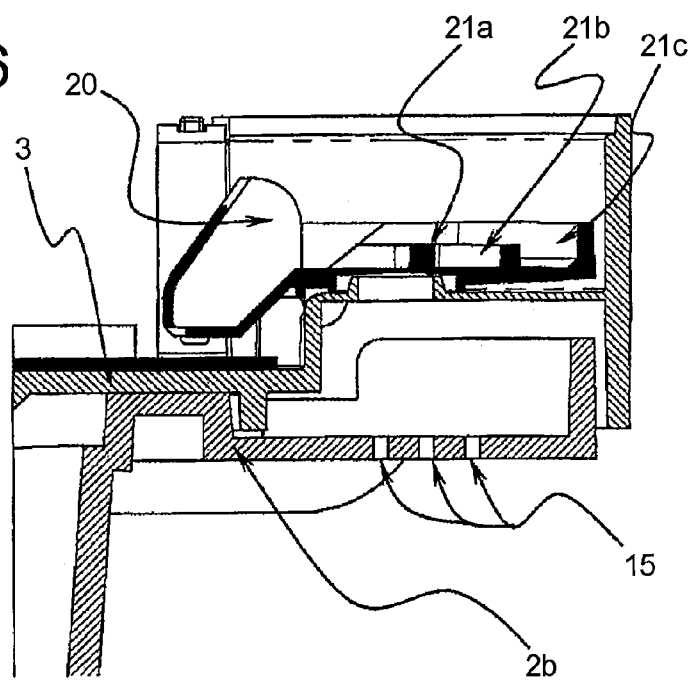
FIG. 6 provides an illustration of a cross section of an embodiment of the device in which the trap 20 is closed during normal operation.
Figure 7:
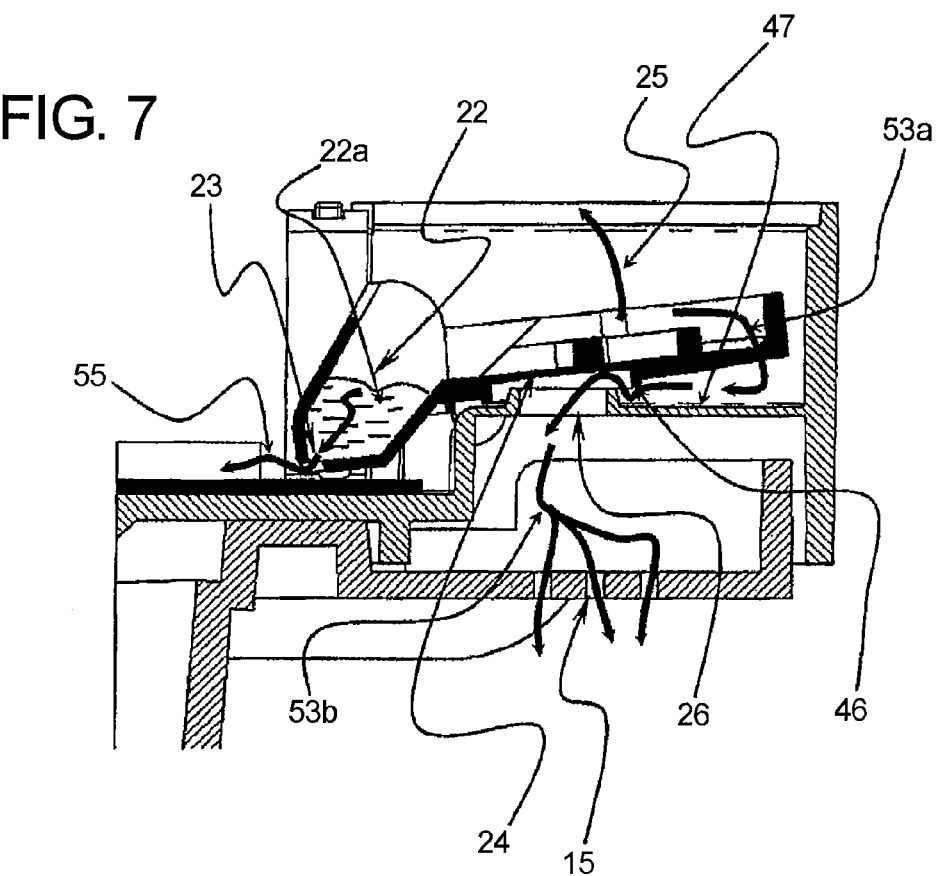
FIG. 7 provides an illustration of a cross section of an embodiment of the device in which the trap is closed during normal operation.
Figure 8:
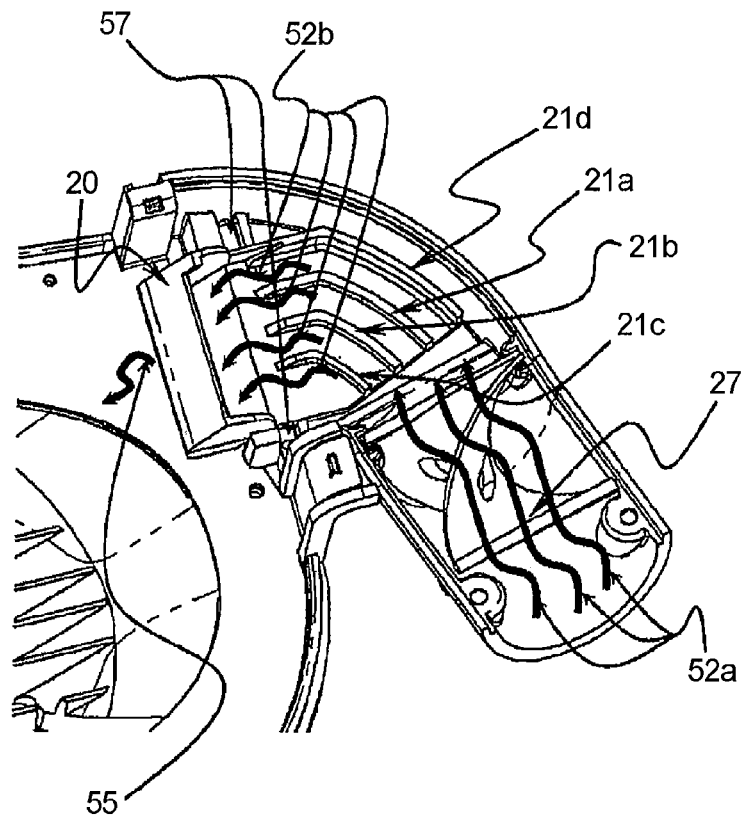
FIG. 8 provides an illustration of a cross section of an embodiment of the device having a trap 20 and helix 27 in apposition showing abnormal flow as a result of an attempt to fill the device 1 through the outlet nozzle 12.
Figure 9:
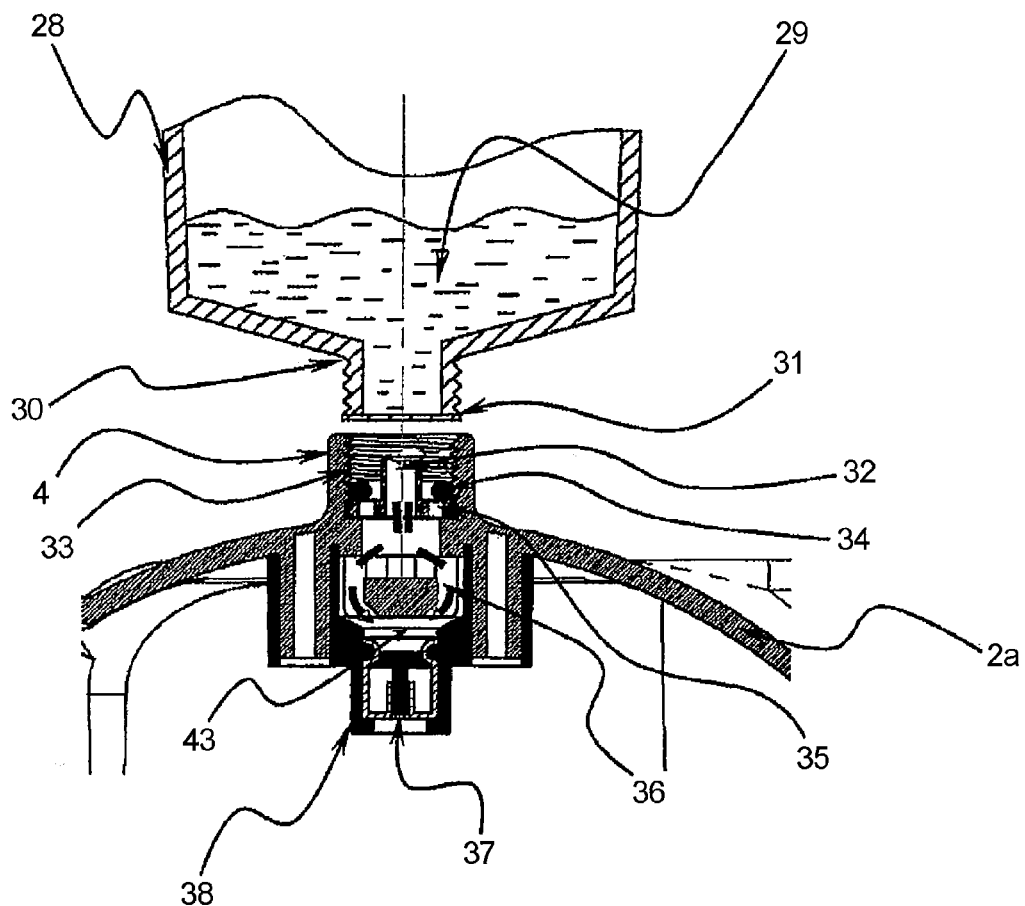
FIG. 9 provides an illustration of a cross-section of one embodiment of the device filling mechanism.
Figure 10:
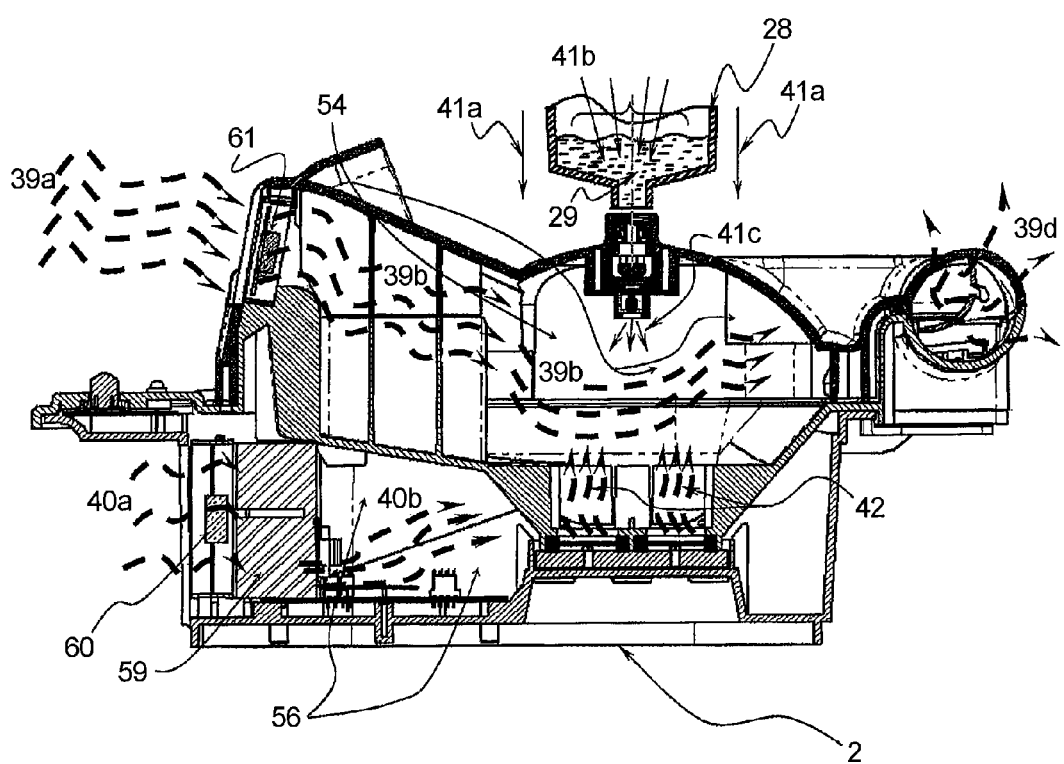
FIG. 10 provides an illustration of a cross section of one embodiment of the device 1 illustrating both a fluid flow and an air flow.
Figure 11:
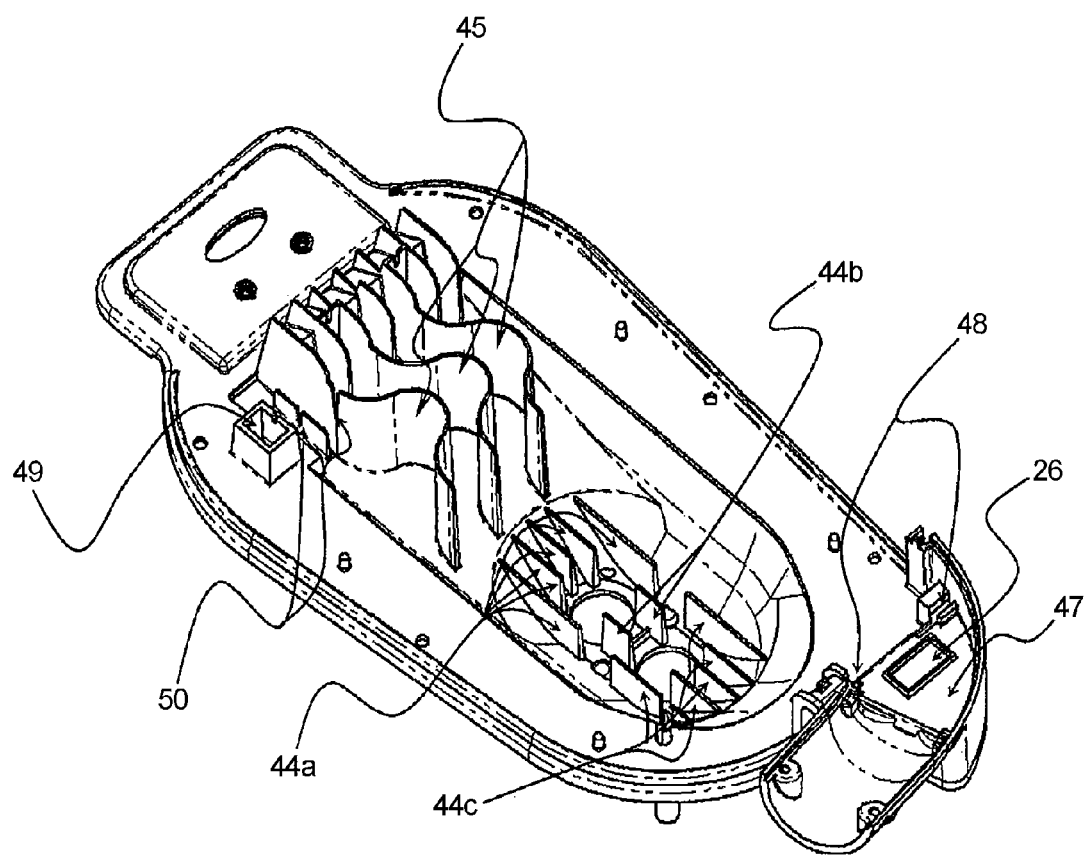
FIG. 11 provides an illustration of an embodiment of an anti-splash guard 45 and an anti-foam guard 44(a-c).
Figure 12:
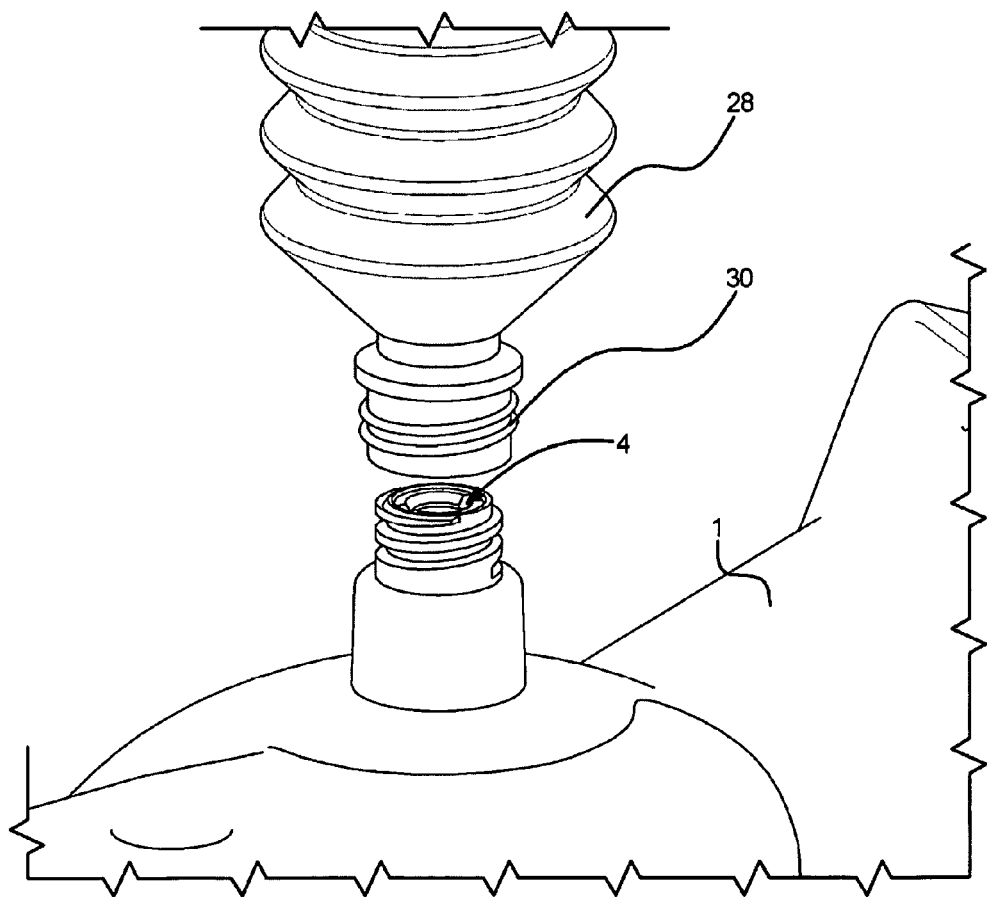
FIG. 12 provides an elevated perspective view of a refill container 28 in close proximity to an inlet 4.
Figure 13:
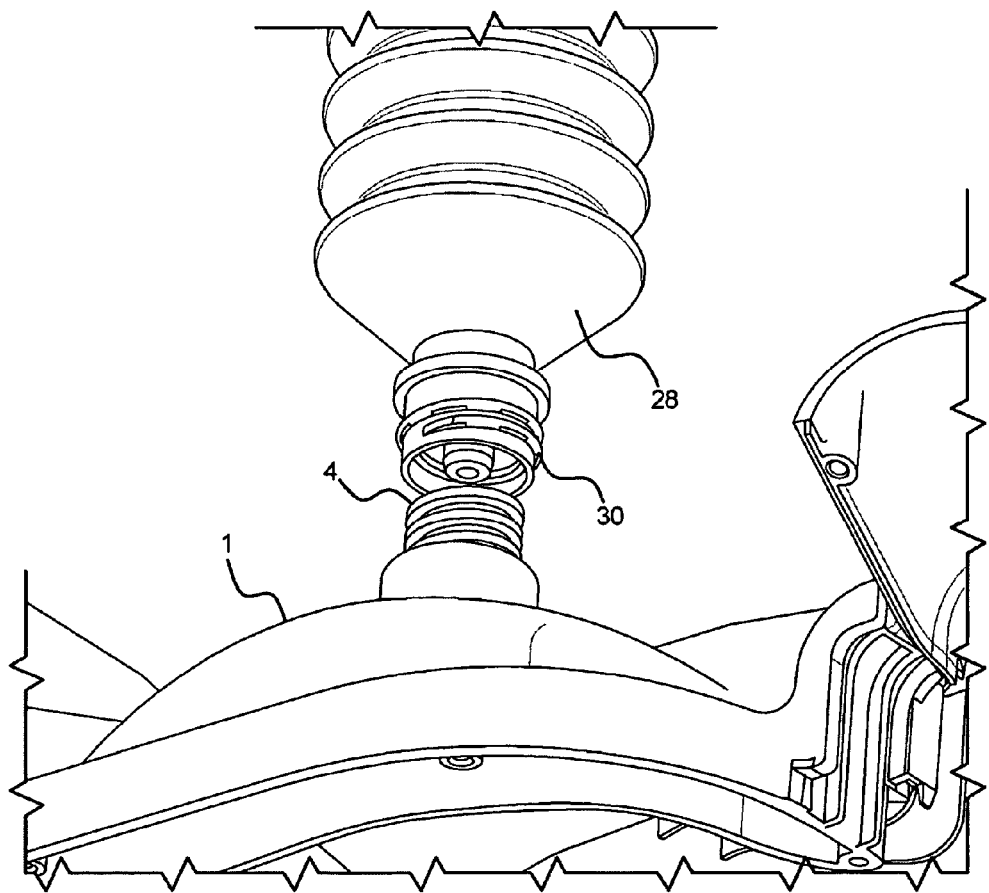
FIG. 13 provides a perspective view of a refill container 28 in close proximity to an inlet 4 from beneath the inlet 4.
Figure 14:
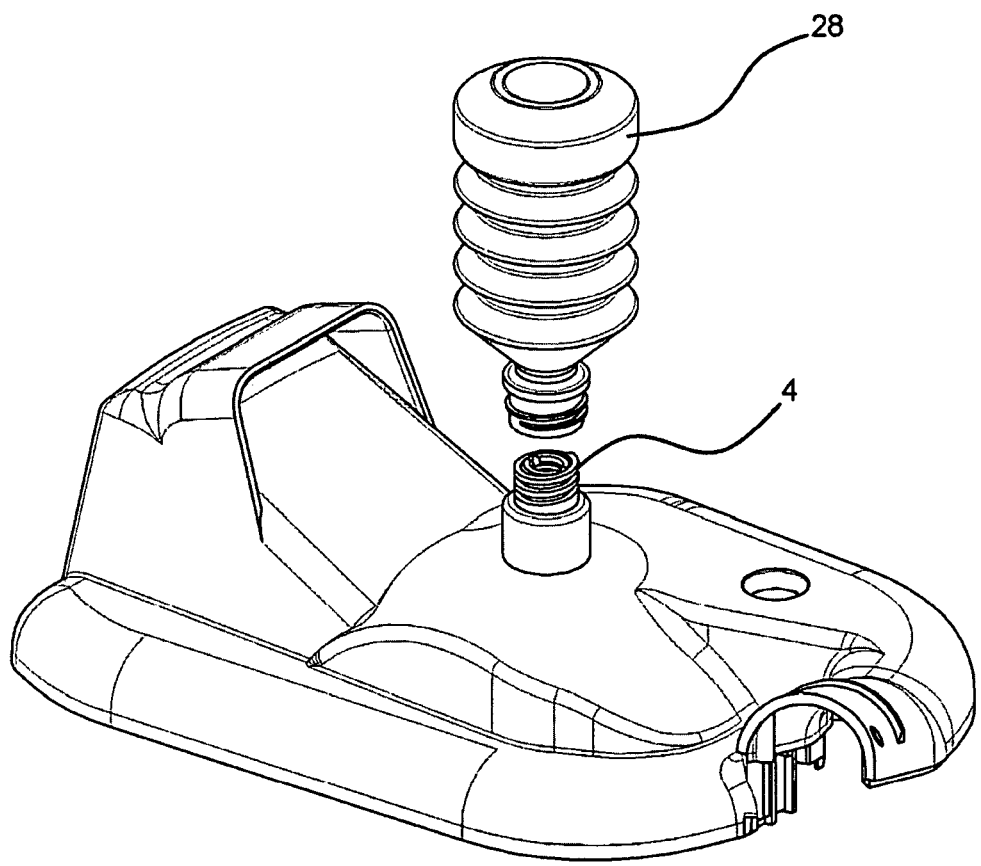
FIG. 14 provides an elevated perspective view of a refill container 28 in close proximity to an inlet 4.
Figure 15:
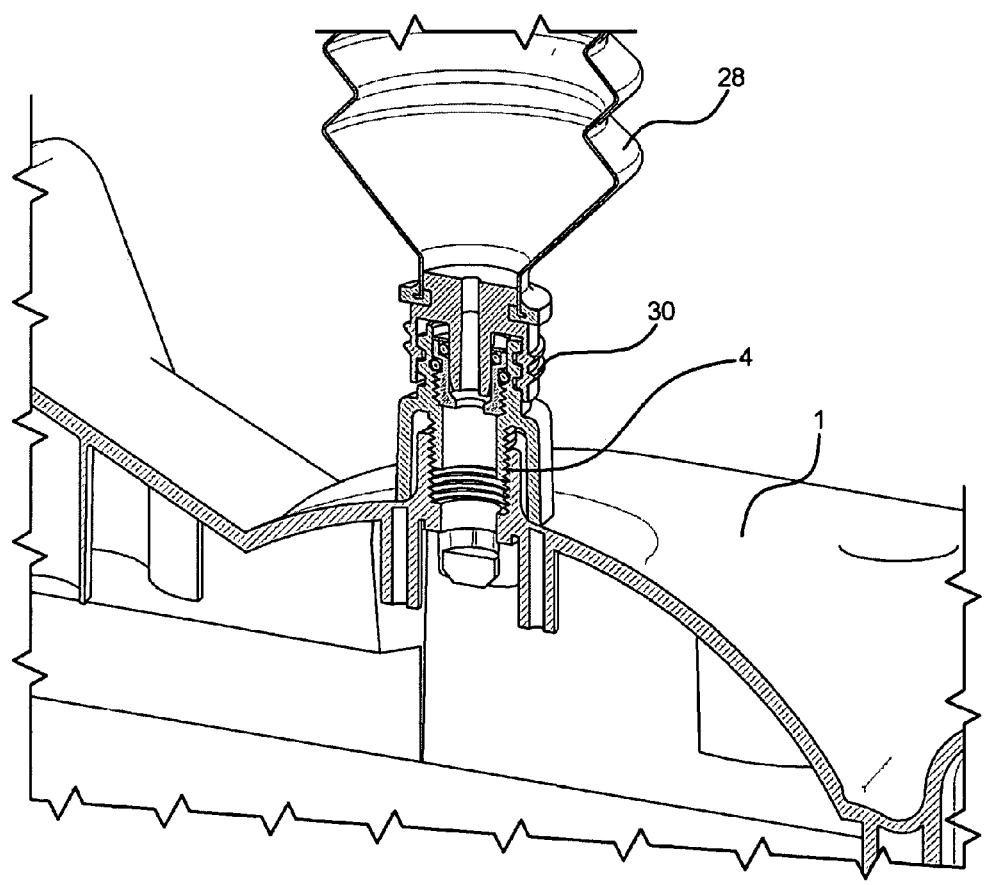
FIG. 15 provides a cross section view of a refill container 28 in close proximity to an inlet 4.

For purposes of the present application the phrase "mist-generating" refers to the conversion of a liquid into very small droplets, which are expelled from the unit looking as fog, vapor, fume, fine spray, or having other visual similarities.

The abbreviation "AC" refers to alternating current which is normally above 90 volts and which is typically available from electrical wall outlets and in some cases from special power supply stations or converters.

The abbreviation "A/C" refers to Air Conditioning.

The abbreviation "LVDC" refers to low voltage direct current as provided by a vehicle power supply, typically from an accessory receptacle or directly from the battery and between 10 to 26 volts The abbreviation "VOCs" refers to volatile organic compounds, such as aldehydes, ketones, hydrocarbons and the like. They can be expelled by some substances and materials, which in some cases raises health concerns. VOCs are often the cause of "new car smell" as new materials, due to their chemical process of manufacture and/or finish continue expelling these odors even after months of reaching the end-customers.

Referring to FIGS. 1 to 15, a first embodiment of a mist-generator 1 (also referred to at various points herein as device, nebulizer, atomizer and cold fogger) is disclosed that is useful for automotive mold, bacteria and odor treatment and removal. The device can operate from a vehicle's 12 or 24 volt direct current electric power supply through a power adapter 7. Because the disclosed mist-generating device 1 can be powered by a LVDC power supply, the risk of shock is greatly reduced as compared to devices that are powered by AC. This is particularly significant because the fluid used for the cleaning is often an electro conductive liquid composition. The mist-generator 1 includes a top cover 2a and a bottom cover 2b that connect at a seal 3 to form connected covers 2. As shown in FIGS. 1, 5, 8, and 11, the top cover 2a is aligned with bottom cover 2b via respective keys 19 and 49. Respective tab pairs 48, 50, and 57 secure the covers 2a and 2b together. A button 9 may be pushed to separate covers 2a and 2b. The top cover 2a may include a handle 6 to enable the mist-generator 1 to be lifted by a user.

In this embodiment no wires leading from the vehicle are needed because a LVDC power source is typically available inside the cabin of most vehicles. The point of electrical connection inside the vehicle cabin can be a cigarette lighter or similar accessory electrical outlet. In this configuration the risk of a power cord being pinched, short circuited or cut is completely avoided as are gaps in doors or windows that are necessary when known devices are used. Thus, undesired leaks of the cleaning solution's mist are also avoided.

In an embodiment, a mechanism can be provided in the device that prevents the introduction of undesired objects or unknown chemicals into the device. To this end, the device 1 can be configured with a unique filling mechanism 4, shown in more detail in FIG. 9, that allows only specific refill containers 28 to be attached to the device; containers specifically designed for use with the device 1. An external locking mechanism, such as threading can be located on a neck 30 of the container that makes up the orifice. The orifice can be used to expel the cleaning fluid 29 from the container into the mist generator 1. Filled refill containers 28 can be covered by a thin material 31, such as a foil, during transportation and storage prior to their use such that the cleaning solution is held in place in the tube and is not contaminated.

The atomizer-nebulizer-cold fogger device 1 can have an inlet 4 adapted to receive the locking mechanism, such as the threaded neck 30 of the refill container 28. Thus, a neck 33 of the inlet 4 could be threaded 34 such that a threaded refill container 28 could be screwed into the inlet 4. The inlet 4 can also be adapted with a cutter 32 that pierces the foil 31 and allows for the fluid 29 to pass from the refill container 28 into the mist generator device 1 after refill container 28 is screwed onto the inlet 4 (as noted by arrow 41a). Preferably, cutter 32 is configured to prevent the foil from being shredded into pieces so that chips of the foil will not fall into the sprayer or clog the inlet 4 of the device 1. The cutter 32 can be mounted to inlet 4 using the same threading 34 that the refill container 28 uses and can be screwed into the inlet 4 until it bottoms down at section 35. Cutter 32 can have a passage inside the cutting edge that allows the fluid 29 to pass through once the container 28 has been pierced. In an embodiment the threading on the neck 30 of the refill container 28 can be inside the neck 30 such that the neck 30 screws into an externally threaded inlet 4 on the machine 1. Under the cutter 32 and inlet 4 the device 1 can have a check valve 16, 36-38, and 43 that prevents fluid entry by gravity. In such an embodiment, positive pressure must be applied to the refill container 28 to force liquid 29 and 41c into the storage chamber 54 (FIG. 10) of the mist generator 1. In one embodiment, the refill container 28 can simply be squeezed around area 41b, such as in tube type refill containers 28.

Refill container 28 can be any type of container that can hold the mist solution 29 such that it can be introduced in to the mist-generating machine 1. Refill container 28 can have any shape and be made of many materials including pliable plastics and metals. One exemplary shape is similar to a tube, such as a toothpaste tube, having an orifice on one end and closed on the other. Squeezable tubes, bottles, cans, bags can be used so long as they are adapted to lock in to the machine. Many other collapsible or flexible containers are known and can be used to refill the mist generator so long as they are adapted to include the same neck-locking design 30. Alternatively, pressure can be applied to the device 1 using a syringe type refill container or a caulking-gun concept in combination with the locking mechanism.

The mist generator 1 has a spray outlet 12 of sufficient size to allow enough mist to come out to cleanse an automobile interior and ventilation system. The size of the outlet 12 opening allows for the possibility that undesirable solutions or foreign materials could gain entry into the misting chamber 54. To avoid this, as best illustrated in FIGS. 6-8, the device can be configured with a trap 20 that involves a moving piece inside the machine 1. Such a trap 20 can have a horizontal axis and two protrusions 46 that emerge from the body of the trap 20. The protrusions 46 serve as a pivoting point for the trap to flip up, as in FIG. 7 and down, as in FIG. 6. At one of the sides of the axis, there can be one or more small volume receptacles 22 with one or more holes 23 at the bottom. The other side can be flat. As best illustrated in FIG. 8, the flat part can have at its top surface one or more ridges 21*a-d* that direct any fluid 52*a*, 52*b*, and 53*a* coming from the inlet over the axis and into the receptacle 22. On its bottom, the trap 20 has a ridge 24 and surface that closes an opening 26 on the bottom surface of the sprayer. As best illustrated in FIGS. 6 and 7, the receptacle 22 can be designed in such a way that as fluid 22*a* accumulates in it will lower down as the weight of the fluid forces it down and then will retain more fluid 22*a* as it lowers. In the embodiment shown in FIG. 7, the receptacle 22 stops lowering as soon as it makes contact with another part or surface of the device. When this happens, the flat part of the trap 20 rises as the trap 20 flips over its axis shafts. As the flat part rises (as noted at numeral 25), the opening 26 on the device 1 is uncovered and most of the fluid 53*b* being poured spills out of the device 1 at vents 15 of bottom cover 2*b* via section 47. As long as the fluid flow keeps sufficient pressure against the bottom surface of the trap fluid 53*b* will flow through the device's opening 26. After the fluid flow stops, the receptacle 22 of the trap 20 loses weight as the fluid 22*a* and 55 goes through the small orifice and the trap 20 tilts back to its original horizontal position to seal the opening 26 of the device.

In an embodiment best shown in FIG. 8, a helix shaped piece 27 can be included in the spray nozzle 12 such that air and mist can come freely out of the spray nozzle 12 but the entry of objects into the device such as those that could be used to maintain the trap 20 closed, is precluded.

The device 1 can include more than one blower 60 and 61 in FIG. 10. Separate blowers 60 and 61 can be positioned in separate chambers. In one chamber 56, one or more blowers 60 can be used to push air 40*a*-40*d* over the electronics 59 to keep them cool, and in a separate chamber 54 where the mist 42 is produced, a separate set of fans 61 can be used to pull in air 39*a* via vent 13 to spray the mist 39*b*-39*d* and 42 out of the device 1 through the outlet 12. By maintaining separate chambers the risk of having the fluid contacting the electronics is reduced and there is a lower probability of a short circuit or shock.

In an embodiment best illustrated in FIG. 11, the bottom cover 2*b* of the spray device 1 can have an internal structure in the misting chamber 54 that reduces turbulence and splashing. Such a mechanism helps maintain performance of the delicate components and mechanisms in the chamber 54. The anti-splashing and anti-foaming features can be a set of ribs 45 and 44*a-c* around the piezos transducers 106 (that generate the mist 42) that will act as wave-breakers and will reduce the turbulence of the fluid levels above the piezos 106, which in turn helps to maintain a consistent output of mist. The device can have a series of "S" shaped ribs 45 that allow air to pass through, but doesn't allow splashing or water displacement which normally occurs in a straight line.

The device 1 can include a level vial as best shown in 5 of FIG. 1 which can be positioned at the top surface 2*a* to let a user know when the machine is level or within an acceptable inclination in which the machine will work correctly. This helps to prevent the user from placing the machine at an angle that may reduce the performance characteristics of the device 1.

The device may also have an electrical interlock to prevent the mist generator 1 from operating if the angle is outside an acceptable range.

The spray device 1 can also include a mechanism for notifying the operator that the treatment is in progress, finished or when there is a problem with the machine. The mechanism can be a top display 8 with light(s) 10 and 11, such as LED's, which shows the status of the machine and/or the treatment without having to open the door of the car. Depending of the frequency of the flashing, the user can determine if the machine is still running or is stopped because the treatment time was complete, or whether there was a problem with the machine. The display 8 can also be a readable display that describes the sprayer status or it can be a remote wired or wireless display showing or having indicator lights or a readable display. Such a display can be placed either inside of the vehicle in a visible place or placed outside of the vehicle at a convenient location where the user can conveniently observe it. The device 1 can be configured with a sound system 51 such that an attached or remote buzzer can indicate the status of the machine or the stage of the treatment. In an embodiment, the light emitting source 10 and 11 can be used that emits light beams through the mist to show the effectiveness of the treatment to the user(s).

The disclosed spray device provides an easily controllable sprayer in a reduced size, that can produce a very fine spray of cleaning solution, comparable to a mist. The spray molecule size is much smaller than water allowing better penetration of seats, headliners, carpets and small orifices in the A/C system components.

In one embodiment a portable piezo-based, mist-generating device 1 is provided that can connect to a vehicle's Low Direct Current Voltage (LDCV) power supply in order to perform cleaning/odor removal services on exposed and hard-to-reach surfaces of the interior of a car. The device 1 can incorporate a unique filling system, which prevents foreign material from entering into the unit, including fluids or substances that would deteriorate the performance of the unit or the components of the device 1 itself. It can utilize an automatic timed shut-off circuit, a fluid level indicator/window 14 and a positioning level indicator 5. The inside of the device can include an internal anti-foam and anti-splash structure designed to keep electronic components dry and reduce the foaming and turbulence of the fluid being misted. It can also include a metal plate within a plastic embodiment to increase ultrasonic transducer 106 performance.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

Figure 16:
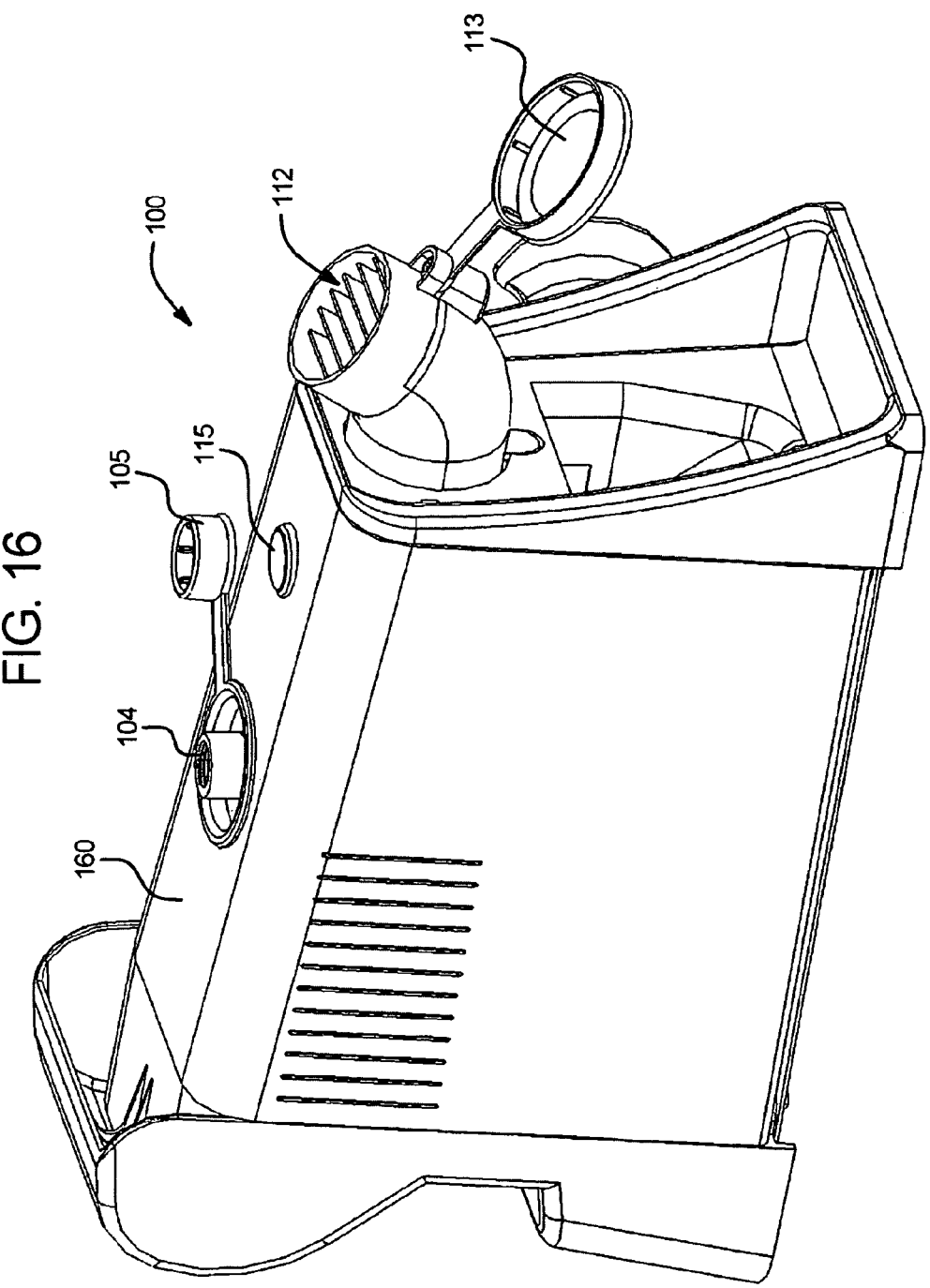
FIG. 16 provides a perspective view of another embodiment of the device 1.
Figure 20:
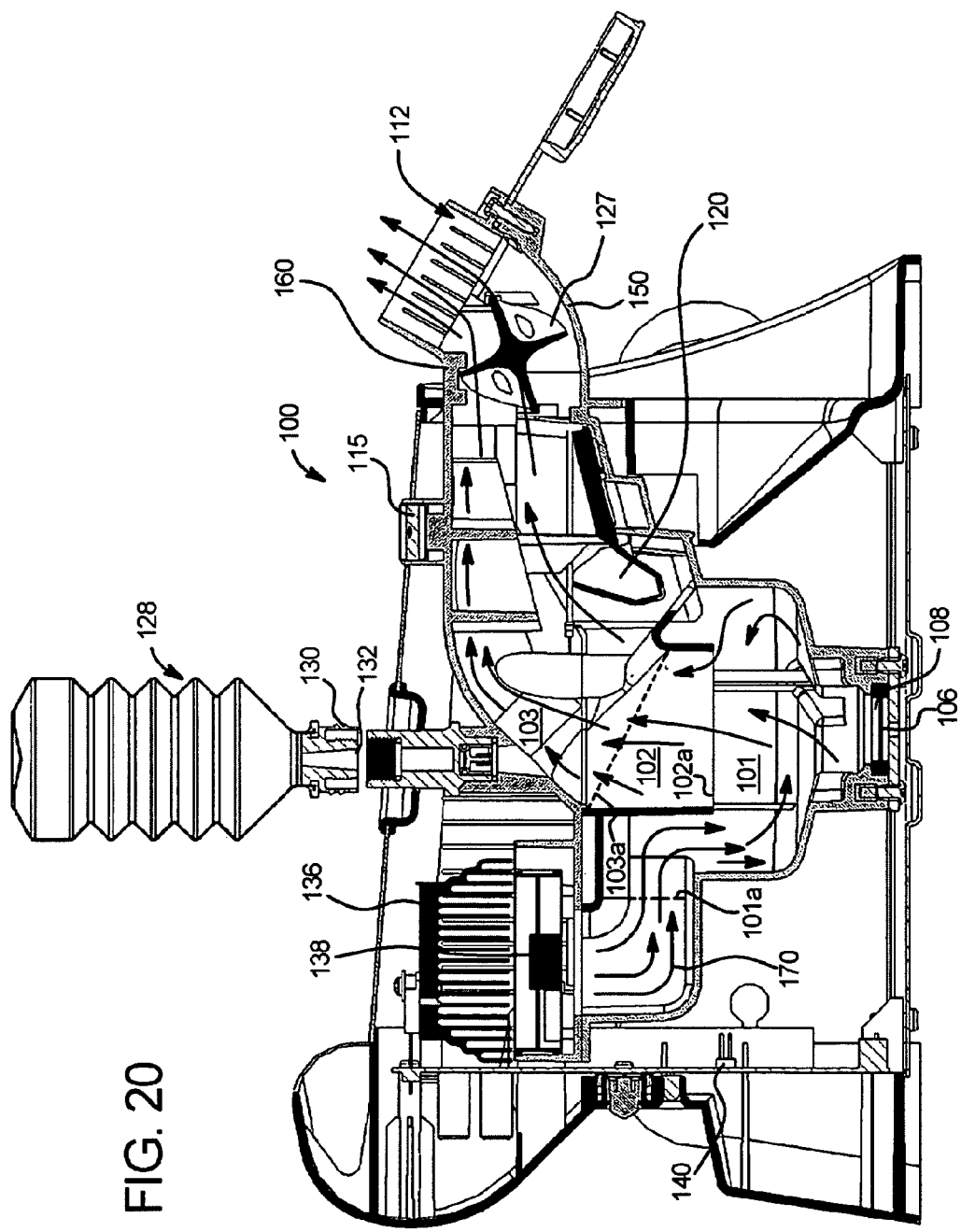
FIG. 20 provides a side view of the inner contents of the device 100 including arrows illustrating air flow through the device.

Referring now to the embodiment of FIGS. 16 to 22, a mist-generating device 100 is disclosed. The device 100 includes a cover 160, which covers the inner components of the device 100, as illustrated in FIG. 16. A unique filling mechanism 104 prevents the introduction of undesired objects or unknown chemicals into the device. The filling mechanism 104 allows only specific refill containers 128, such as that illustrated in FIG. 20, to be attached to the device 100. An external locking mechanism, such as threading 130 can be located on a neck of the container that makes up the orifice 132 of the refill containers, as illustrated in FIG. 20. The orifice can be used to expel the cleaning fluid from the container 128 into the mist generator 100. Filled refill containers can be covered by a thin material 31, as in FIG. 9, such as a foil, during transportation and storage prior to their use such that the cleaning solution is held in place in the tube and is not contaminated. It should be appreciated that the thin materials 31 may be any suitable material.

Referring to FIG. 16, in one embodiment, the device 100 includes a cap 105 configured to cover the filling mechanism 104 when the device is not in use. In this embodiment, the cap includes ridges which create resistance against the outside of the filing mechanism 104, holding the cap 105 in place. It should be appreciated that in various embodiments, any suitable cap may be used with the device 100.

The device 100 can operate from a vehicle's 12 or 24 volt direct current electric power supply through a power adapter 107. Because the disclosed mist generating device can be powered by a LVDC power supply, the risk of shock is greatly reduced as compared to devices that are powered by AC. This is particularly significant because the fluid used for the cleaning is often an electro conductive liquid composition.

In this embodiment no wires leading from the vehicle are needed because a LVDC power source is typically available inside the cabin of most vehicles. The point of electrical connection inside the vehicle cabin can be a cigarette lighter or similar accessory electrical outlet. In this configuration the risk of a power cord being pinched, shorted circuited or cut is completely avoided as are gaps in doors or windows that are necessary when known devices are used. Thus, undesired leaks of the cleaning solution's mist are also avoided. Also, low current consumption of the device allows thinner cable to be used and operation without vehicle running. For instance, in one example, the device 100 uses between 2 to 6 amps and consumes between 2 to 20 ml of treatment fluid per minute on a typical 12 volt system. Many newer vehicles have reduced wire size and smaller battery and charging systems, which limits the current capability of the vehicle. The thin cables used by the device 100 are amenable to such new vehicles and enhance safety.

The atomizer-nebulizer-cold fogger device 100 can have an inlet 104 adapted to receive the locking mechanism 130, such as the threaded or unthreaded neck of the refill container 128. Thus, the inlet 104 could be threaded such that a threaded refill container 128 could be screwed into the inlet 104. The inlet 104 can also be adapted with a cutter, such as that disclosed in conjunction with the device 1 in the former embodiment, that pierces the thin material and allows for the fluid to pass from the refill container 28 into the mist generator device 100 after refill container 28 is screwed onto the inlet nozzle 104. In one embodiment, the threading on the neck of the refill container 128 can be inside the neck such that the neck screws into an externally threaded inlet on the machine. Also, in various embodiments, under the cutter and inlet 104, the device 100 includes a check valve, such as check valve 43 in FIG. 9, that prevents fluid entry by gravity. In such an embodiment, positive pressure must be applied to the refill container 128 to force liquid into the mist generator 100.

Refill container 28 can be any type of container that can hold the mist solution such that it can be introduced in to the mist generating machine. Refill container 28 can have any shape and be made of many materials including pliable plastics and metals. One exemplary shape is similar to a tube, such as a toothpaste tube, having an orifice on one end and closed on the other. Squeezable tubes, bottles, cans, bags can be used so long as they are adapted to lock in to the machine. Many other collapsible or flexible containers are known and can be used to refill the mist generator so long as they are adapted to include the same neck-locking design. Other features a suitable container may posses include: (a) preventing drips when held upside down; (b) preventing refilling (by having a small opening); (c) clearing a check-valve; (d) opening with head space in the container by allowing some air to pass through the valve after the contents have been installed; (e) enabling virtually 100% of contents to be dispensed; (f) enabling a user to view the contents of the container; (g) enabling a user to view the level of contents in the container; (h) any combination of these; and (i) any suitable features. In various other embodiments, pressure 100 could be applied to the device using a syringe type refill container or a caulking-gun concept in combination with the locking mechanism.

Figure 22:
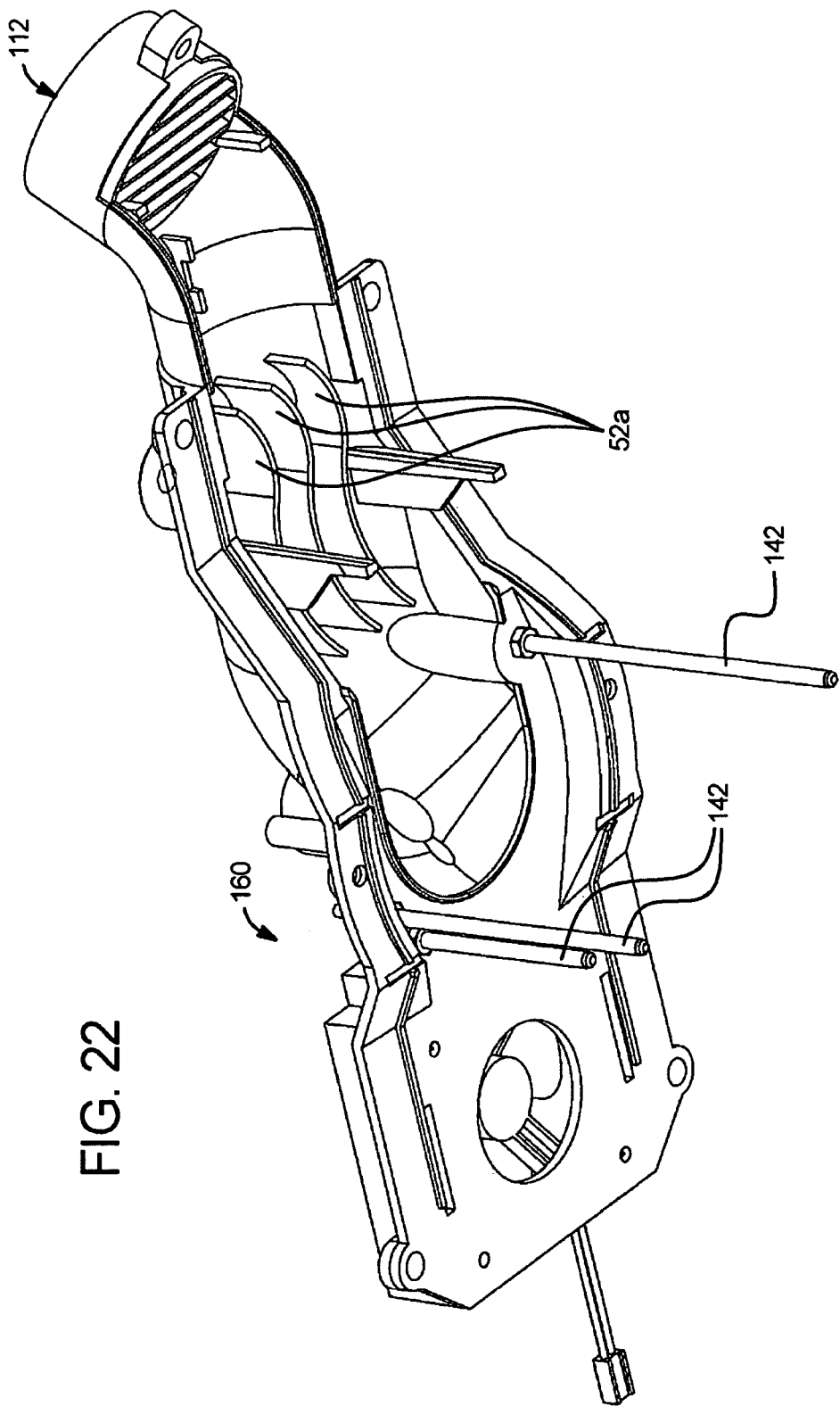
FIG. 22 illustrates an upper assembly defining part of the misting chamber of one embodiment of the device 100.

Referring to at least FIG. 16, the device 100 includes a level 115. The device operates most effectively when it is level. Thus, the level 115 enables a user identify how level the device 100 is when placing it in a vehicle for use. In one embodiment, the level 115 is a known mechanical float or magnet level. In another embodiment, the device 100 uses probes 142, as illustrated in FIG. 22, that send a voltage into the fluid in the misting chamber and measure differential at 3 electrode points. It should be appreciated that in various such embodiments, it would be possible to use two probes and a metal housing as the ground. It could also only have a single probe for low level indication. The use of a third probe substantially eliminates corrosive issues and renders the device 100 more serviceable. Additionally three probes act as a fail safe for excessive tilting as any direction the machine is moved will signal a low or high level sensor. It should be noted that probes could have insulators that would prevent them from any electrical contact. It should be appreciated that in various other embodiments, the level may be any suitable electronic level system, GPS unit, or any suitable type of level.

Figure 21:
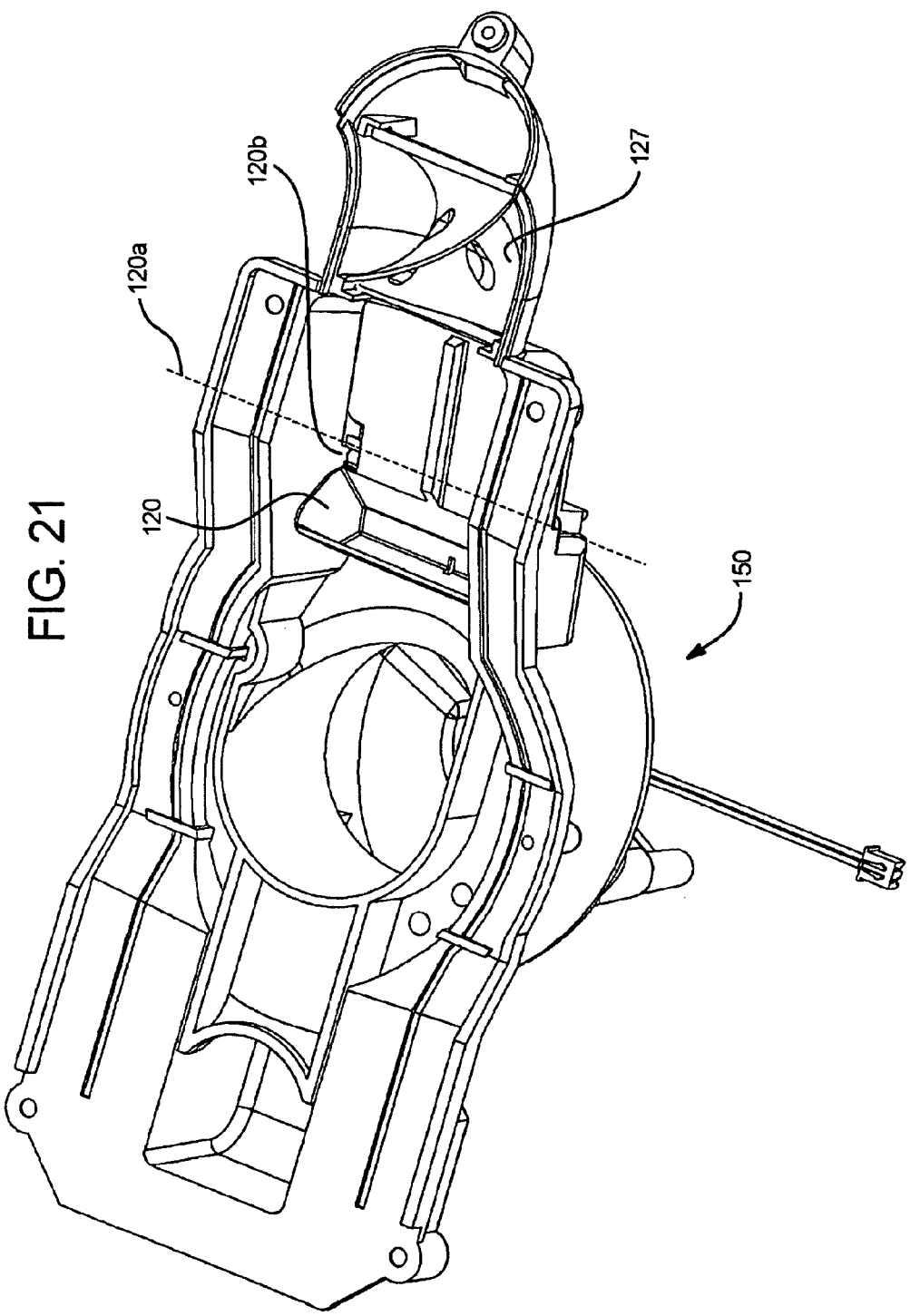
FIG. 21 illustrates a lower assembly defining part of the misting chamber of one embodiment of the device 100.

Referring now to FIGS. 20 to 22, the device 100 includes an upper assembly 160 and a lower assembly 150 that define a misting chamber including three separate but adjacently conjoined areas: area one 101, area two 102 and area three 103. The air flow parameters for the misting chamber of the device 100 are governed by the these areas. For illustrative purposes, vectors 170 in FIG. 20 illustrate the flow of air through the device 100.

Referring to FIG. 20, area one 101 is generally defined by the area between boundary 101a and boundary 102a. Area one 101 includes a piezo actuator 106 configured to atomize misting solution which enters the misting chamber through the filling mechanism 104 from the container 128. To further facilitate and maximize the atomizing effect in area 101, the piezo actuator 106 is placed at the bottom of a tube or column 108 of misting solution thus creating a choking effect above the piezo actuator 106 during its operation. Based on a simple linear stress equation, Stress=Force/Area (S=F/A), the column of fluid effect above the piezo actuator 106 being the same diameter as the piezo actuator 106 at a predetermined height allows all actuating forces (F) generated by the piezo actuator 106 during operation of the device 100 to be generated over a specific area (A) of fluid. The resultant stress (S) generated in the fluid based on the force exerted (F) over a given area (A) creates turbulence in the fluid thus resulting in the maximum controlled amount of movement possible of the fluid thus maximizing the atomizing effect. In one embodiment, the piezo actuator 106 is angled so it is not perpendicular to the column of fluid. This further intensifies and increases the perpendicular force vector (magnitude & direction) generated from the piezo face with respect to the fluid volume. It should be appreciated that in various embodiments, the piezo actuator 106 may be situated in any suitable manner.

In traditional piezo systems, a potentiometer is mechanically adjusted to set the current at a given time. It should be appreciated that device 100 includes a memory device storing a plurality instructions (or software) programmed to constantly monitor and self-adjust voltage and current to the piezo actuator 106. As ambient temperature and voltage fluctuate or resistance increases, the piezo actuator 106 performance will not be optimized. Keeping the input current and voltage constant and optimized under all conditions makes the piezo actuator 106 more durable and its performance more stable. An additional benefit of the use of self-adjusting voltage and current to the piezo actuator 106 is that the potentiometer does not need to be set during manufacturing (i.e. a mechanical potentiometer does not need adjusting).

Referring again to FIG. 20, area two 102 is generally defined by the volume between boundary 102a and boundary 103a. Area three 103 is generally defined by the volume between boundary 103a and outlet 112. Referring to FIGS. 21 and 22, views of upper assembly 160 and lower assembly 150, which define the misting chamber, essentially, when taken apart, the volume inside lower assembly 150 comprises area one 101 and area two 102. The volume inside upper assembly 160 generally comprises area three 103.

The design of the boundaries between areas 101, 102 and 103 control the flow of air and atomized fluid by utilizing a change in the cross-sectional area at each of the boundaries. By Bernoulli's principle, a decrease in cross-sectional area from one section to the next will bring an increase in the velocity of the air/fluid mixture and a subsequent reduction in static pressure, whereas an increase in area will cause a decrease in velocity and an increase in static pressure.

As the cross-sectional area decreases while the mixture moves from area 101 to area 102, the velocity of the fluid increases and the static pressure decreases, causing a Venturi effect which helps to draw the atomized particles away from the fluid in it's liquid state. As the area increases from area 102 to area 103, the velocity of the fluid decreases and the static pressure increases. This increase in static pressure allows the fluid mixture to propel itself through the remainder of the passageway and exit the machine in a controlled condition. The fine tuning of the areas and exit geometry inherent in this invention greatly assists in the atomization process and expulsion of the mixture from the device.

The design of the misting chamber of device 100 maximizes the efficiency and effectiveness of airflow through the device. Atomized misting solution accelerates through area two 102, enabling the atomization of further misting solution and is decelerated by the expanse of volume in area 103, such that it may exit the outlet 112 at a proper pace in a suitable manner.

The mist generator 100 has a spray outlet 112 of sufficient size to allow enough mist to come out to cleanse an automobile interior space and ventilation system. The size of the outlet 112 opening allows for the possibility that undesirable solutions or foreign materials could gain entry into the misting chamber. To avoid this, as best illustrated in FIGS. 20-21, the device can be configured with a trap 120 that involves a moving piece inside the machine, similar to trap 20 in FIG. 6. The trap 120 includes a horizontal axis 120a and two protrusions 120b that emerge from the body of the trap 120, as illustrated in FIG. 21. It should be appreciated that each of features and descriptions related to the trap 20 and its related components in FIGS. 5 and 6 regarding device 1, apply may be incorporated into device 100.

As illustrated in at least FIG. 16, in one embodiment, the device includes a cap 113 configured to cover the spray outlet 112 when the device is not in use.

As illustrated in FIGS. 20 and 21, a helix shaped piece 27 can be included in the spray nozzle 112 such that air and mist can come freely out of the spray nozzle 112 but the entry of objects into the device such as those that could be used to maintain the trap closed, is precluded.

Figure 17:
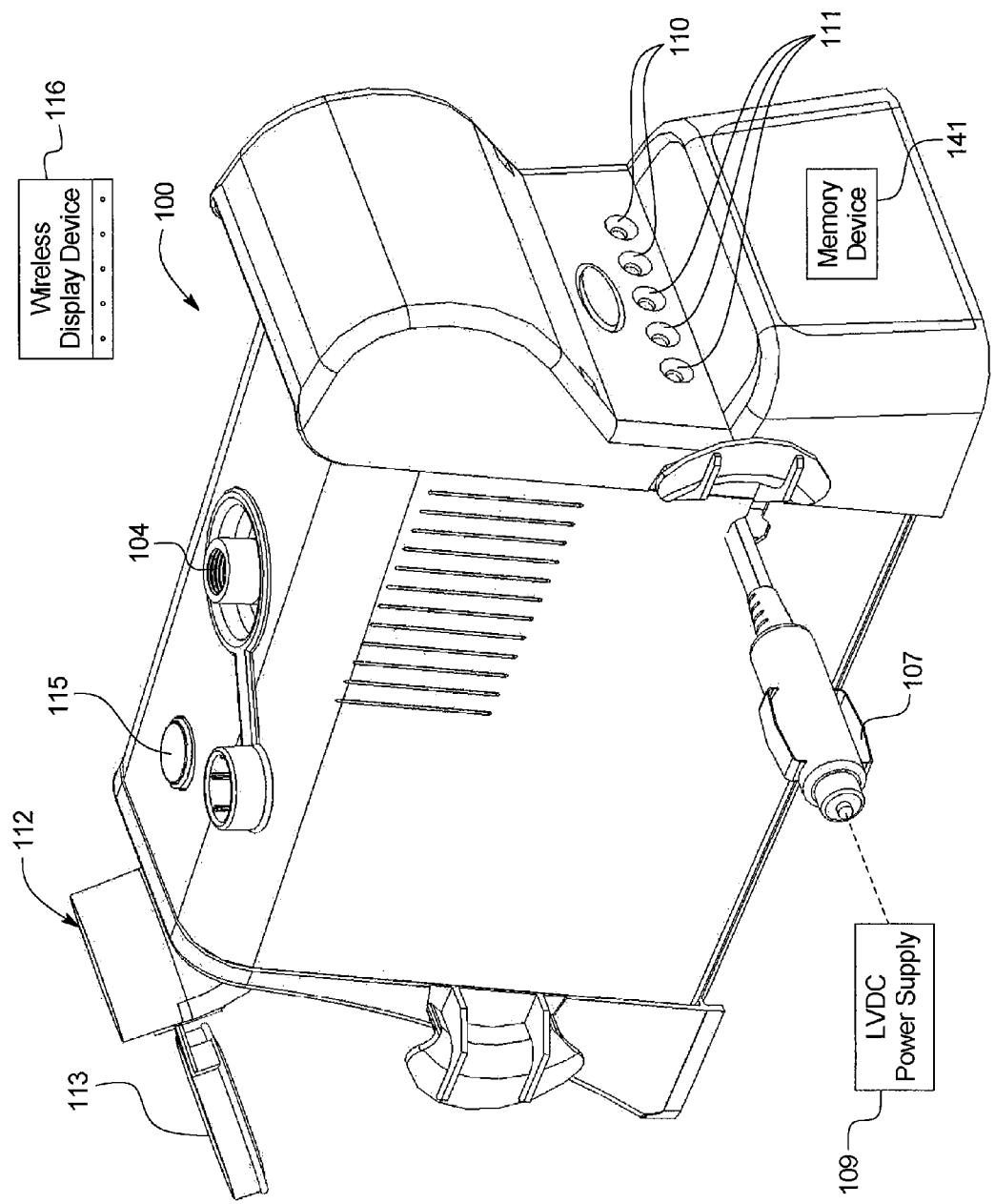
FIG. 17 provides an alternate perspective view of another embodiment of the device 100.
Figure 18:
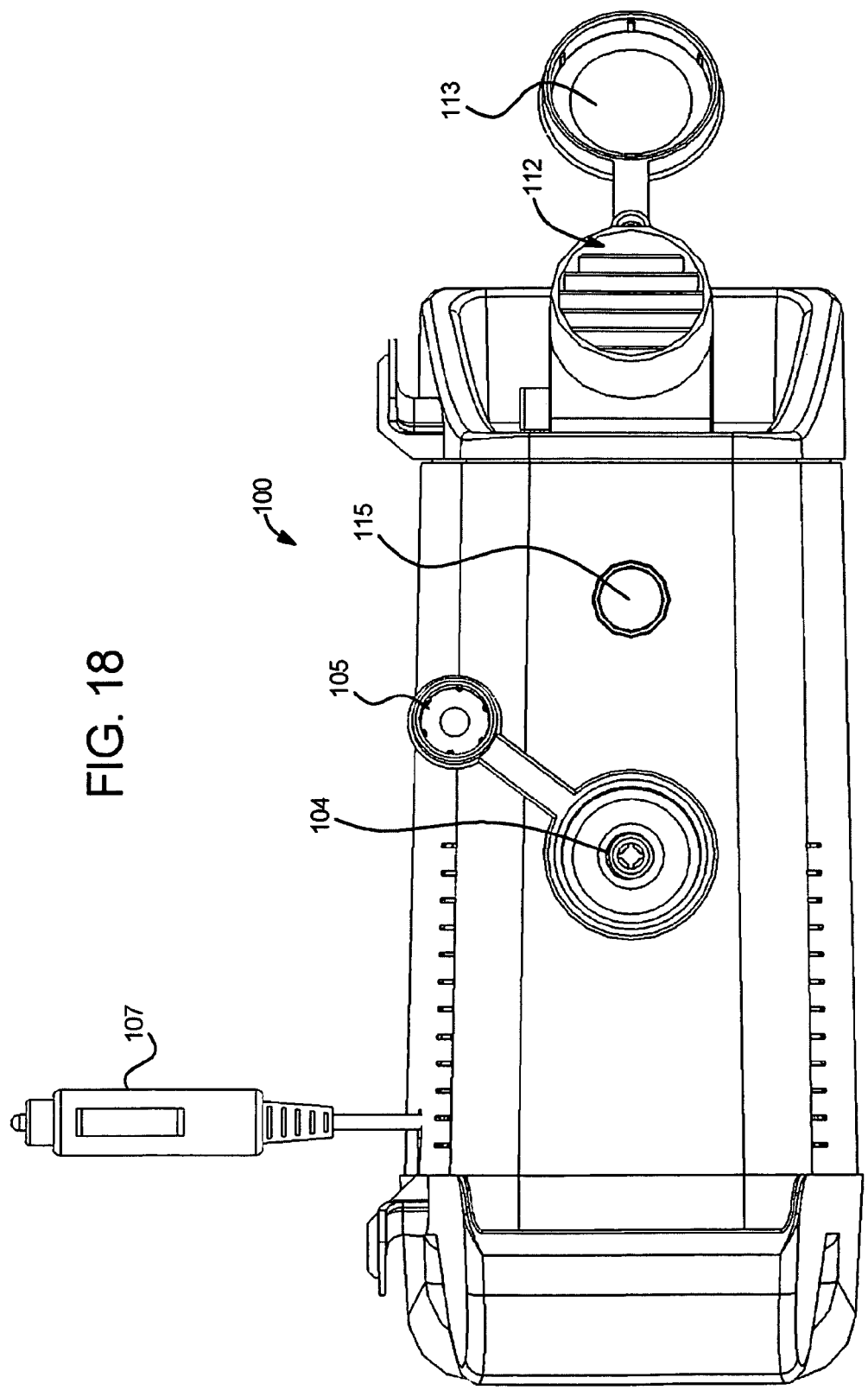
FIG. 18 provides a topographical view of another embodiment of the device 100.
Figure 19:
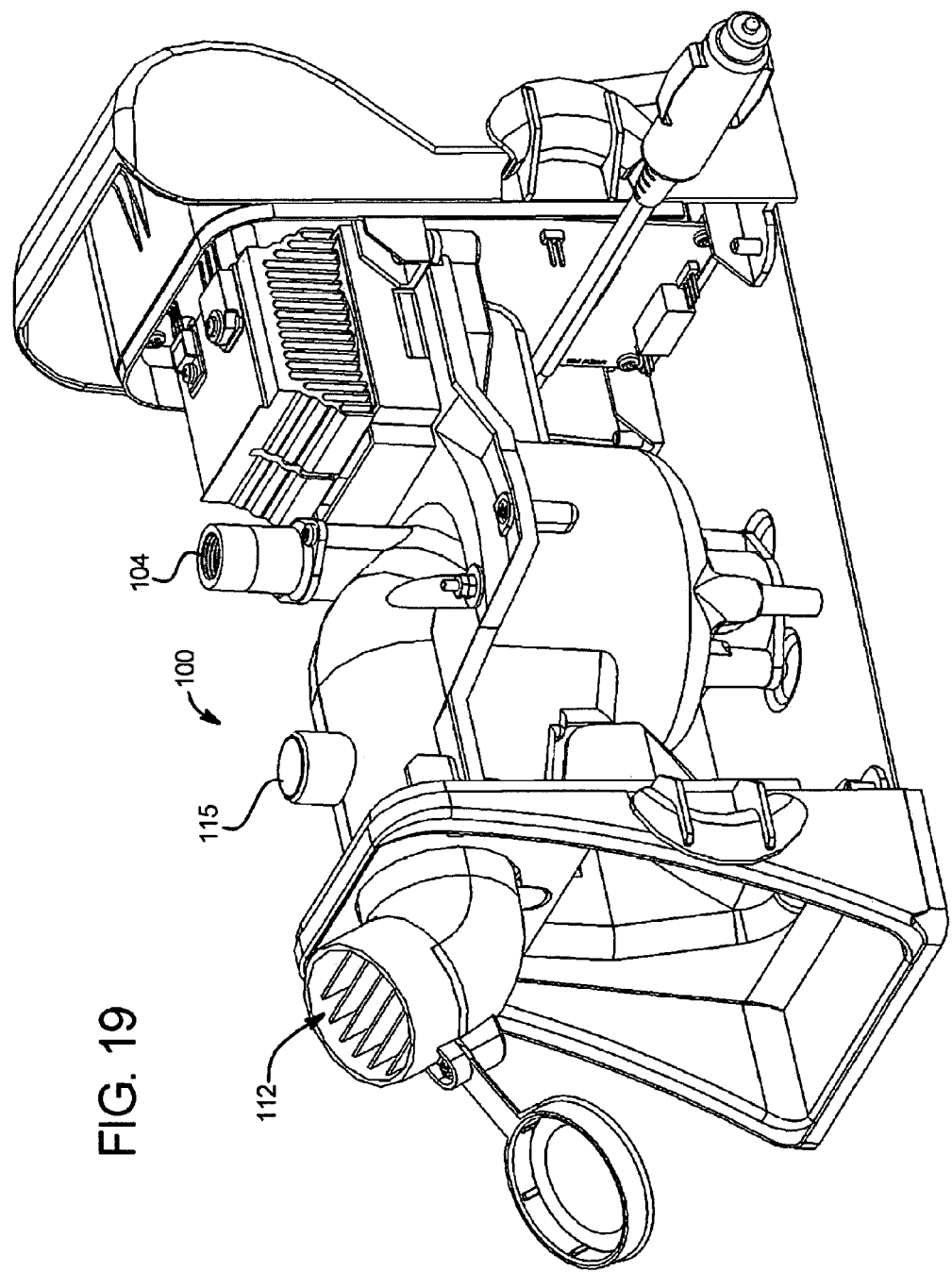

In various embodiments, the device 100 can also include a mechanism for notifying an end user that the treatment is in progress, finished or when there is a problem with the machine. The mechanism can be a display with light(s) 110 and 111 as illustrated in FIG. 17, such as LED's, which show the status of the machine and/or the treatment without having to open the door of the car. Depending of the frequency of the flashing, the user can determine if the machine is still running or is stopped because the treatment time was complete, or whether there was a problem with the machine. The display can also be a readable display that describes the sprayer status or it can be a remote wired or wireless display showing having indicator lights or a readable display as described in the former embodiment with regard to device 1.

In one embodiment, the device 100 includes a diagnostic port 140 which is configured to connect to any suitable processing device. The memory device of the misting device 100 stores data associated with at least: (a) a number of cycles; (b) error codes; (c) a number of short cycles; (d) services; (e) time; (f) input voltage; (g) piezo current; (h) piezo voltage; (i) ambient temperature; (j) heat sink temperature; (k) machine code; (l) operating status; (run time); and (m) any other suitable data.

In one embodiment, the device 100 includes at least one processor and a memory device storing a plurality of instructions, which when executed by the at least one processor, cause the at least one processor to self manage and constantly regulate voltage and current to the piezo actuator 106.

It should be appreciated that any features discussed in conjunction with any of the embodiments disclosed herein may be used in combination with features of different embodiments disclosed herein. Certain features were only discussed in conjunction with one embodiment for brevity.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A mist generating device comprising:
    a housing defining a misting chamber;
    at least one ultrasonic transducer electrically connected to a power supply such that the at least one ultrasonic transducer generates mist when power is supplied to the ultrasonic transducer, wherein the at least one ultrasonic transducer is configured to atomize a programmed amount of a solution per minute;
    an inlet to the misting chamber;
    an outlet from the misting chamber in fluid connection with the inlet;
    a plurality of adjacent spaces positioned between the inlet and the outlet, the plurality of adjacent spaces including:
        a first space having a first volume fluidly connected to the inlet;
        a second space having a second volume fluidly connected directly to the first space, the second volume being smaller than the first volume; and
        a third space having a third volume fluidly connected directly to the second space and the outlet, the third volume being larger than the second volume, the order of the spaces sequentially from the first space through the second space to the third space driving in part an acceleration of the mist through the mist-generating device; and
    an anti-foam guard including at least two parallel ribs each having an S-shape connected to a base of the housing configured to reduce foaming and splashing of the solution covering the at least one ultrasonic transducer,
    wherein the at least one ultrasonic transducer is located within the first space.

2. The mist-generating device of claim 1, further including a refill container in fluid connection with the device, such that fluid from the refill container can pass into the misting chamber.

3. The mist-generating device of claim 2, wherein the refill container is adapted with a locking mechanism for locking into a second inlet of the mist generating device.

4. The mist-generating device of claim 2, wherein the refill container is adapted with a neck with an external locking mechanism for locking into a second inlet of the mist generating device.

5. The mist-generating device of claim 2, wherein the refill container is adapted with an externally threaded locking mechanism locked into an internally threaded second inlet of the mist generating device.

6. The mist-generating device of claim 2, wherein the refill container is adapted with a neck having an internal locking mechanism for locking into a container inlet of the mist generating device.

7. The mist-generating device of claim 2, wherein the refill container is adapted with an internally threaded locking mechanism locked into an externally threaded container inlet of the mist generating device.

8. The mist-generating device of claim 2, wherein the refill container is a container selected from the group consisting of: a bottle or a can.

9. The mist-generating device of claim 2, wherein the refill container is configured to at least one of: (a) prevent drips when held upside down, (b) prevent refilling; (c) clear a checkvalve; (d) open with head space; (e) enable virtually 100% of contents to be dispensed; (f) enable a user to view the contents of the container; (g) enable a user to view the level of contents in the container; (h) collapse; and (i) enable an air-tight fluid connection.

10. The mist-generating device of claim 1, wherein the at least one ultrasonic transducer is configured to atomize between 2 and 20 milliliters of a solution per minute.

11. A mist-generating device comprising:
    a housing defining a misting chamber;
    at least one ultrasonic transducer electrically connected to a power supply;
    a component configured to operate with the power supply to monitor at least one of a voltage and a current to the at least one ultrasonic transducer;
    a curved ribbed guard including at least two parallel ribs each having an S-shape connected to a base of the housing configured to be in contact with a designated fluid and configured to reduce foaming and splashing of the designated fluid over the at least one ultrasonic transducer;
    an inlet to the misting chamber; and
    an outlet from the misting chamber in fluid connection with the inlet.

12. The mist-generating device of claim 11, further comprising:
    a trap mechanism including a volume receptacle located at a base of the trap mechanism configured to cause the trap mechanism to pivot to the open position when an undesirable solution accumulates in the volume receptacle; and
    an auto-shut-off circuit triggered by treatment time,
    wherein the trap mechanism includes an opening at a bottom of the volume receptacle that is configured to drain the undesirable solution accumulating within the volume receptacle.

13. A mist-generating device comprising:
a housing defining a misting chamber;
at least one ultrasonic transducer configured to atomize a designated fluid, and electrically connected to a power supply;
a memory device storing a plurality instructions which, when executed by a processor, cause the processor to operate with the power supply to monitor or self-adjust at least one of a voltage and a current to the at least one ultrasonic transducer;
an inlet to the misting chamber;
an outlet from the misting chamber in fluid connection with the at least one ultrasonic transducer; and
an anti-foam guard including at least two parallel ribs each having an S-shape connected to a base of the housing configured to be in contact with the designated fluid and configured to reduce foaming and splashing of the designated fluid covering the at least one ultrasonic transducer,
wherein the at least one ultrasonic transducer is configured to operate with the processor, the inlet, and the outlet to atomize a programmed amount of the designated fluid per minute.

14. The mist-generating device of claim 13, wherein the voltage is direct current voltage with a voltage of 12 volts and wherein the power supply supplies 2 to 6 amps of current.

15. The mist-generating device of claim 13, wherein the voltage is direct current within a voltage range of between 10 and 26 volts.

16. The mist generating device of claim 13, further comprising a filling port configured to only allow the designated fluid to enter the mist-generating device.

17. The mist-generating device of claim 13, further comprising a filling port connected to a refill container, wherein the filling port includes a cutter for cutting open a sealed end of the refill container as the refill container is locked into place on the mist-generating device.

18. The mist-generating device of claim 13, further comprising a trap mechanism including:
a protrusion that extends from the trap that enables the trap to pivot between an open and a closed position, and
a volume receptacle located at a base of the trap configured to cause the trap to pivot to the open position when an undesirable solution accumulates in the volume receptacle,
wherein the trap mechanism includes an opening at a bottom of the volume receptacle that is configured to drain the undesirable solution accumulating within the volume receptacle.

19. The mist-generating device of claim 13, further comprising a helix shaped baffle mounted within a nozzle included in the outlet.

20. The mist-generating device of claim 13, further comprising a visual fluid level indicator mounted on the mist-generating device.

21. The mist-generating device of claim 13, further comprising a positioning level indicator mounted on the mist-generating device.

22. The mist-generating device of claim 13, further comprising at least one baffle mounted in the misting chamber.

23. The mist-generating device of claim 13, further comprising an auto-shut-off system that is triggered by treatment time.

24. The mist generating device of claim 13, further comprising a low fluid level sensor.

25. The mist generating device of claim 13, further comprising a tilt-level sensor.

26. The mist-generating device of claim 13, further comprising a visual display to indicate a stage of treatment.

27. The mist-generating device of claim 13, further comprising a remote visual code display to indicate a stage of treatment.

28. The mist-generating device of claim 13, further comprising a readable visual code on a display that indicates a stage of treatment.

29. The mist-generating device of claim 13, further comprising a remote display that notifies an operator of a status of treatment.

30. The mist-generating device of claim 29, wherein the remote display is part of a wireless device.

31. The mist-generating device of claim 13, wherein the misting chamber defines a fluid inlet which is connected to a fluid reservoir, a check valve being mounted between the inlet and the fluid reservoir.

32. The mist-generating device of claim 13, further comprising a plurality of adjacent spaces each having a different volume and positioned between the inlet and the outlet, a sequence of the spaces driving in part an acceleration of a fluid through the mist generating device, wherein the ultrasonic transducer is located within a first space.

33. The mist-generating device of claim 32, wherein the different volumes of the plurality of adjacent spaces create a venturi effect.

34. The mist-generating device of claim 32, wherein the outlet is operatively attached to one of the plurality of adjacent spaces.

35. The mist-generating device of claim 32, wherein a fan adjacent to the inlet drives air into the space housing the at least one ultrasonic transducer.

36. The mist-generating device of claim 32, wherein the voltage is direct current voltage with a voltage of 12 volts and wherein the power supply supplies 2 to 6 amps of current.

37. The mist-generating device of claim 32, wherein the voltage is direct current within a voltage range of between 10 and 26 volts.

38. The mist-generating device of claim 32, further comprising a filling port that is configured to only allow a designated fluid to enter the mist-generating device.

39. The mist-generating device of claim 32, further comprising a filling port connected to a refill container, wherein the filling port includes a cutter for cutting open a sealed end of the refill container as the refill container is locked into place on the mist-generating device.

40. The mist-generating device of claim 32, further comprising a trap mechanism that blocks the entry of an undesirable solution or foreign materials through the outlet.

41. The mist-generating device of claim 32, further comprising a helix shaped baffle mounted within a nozzle included in the outlet.

42. The mist-generating device of claim 32, further comprising a visual fluid level indicator mounted on the mist-generating device.

43. The mist-generating device of claim 32, further comprising a positioning level indicator mounted on the mist-generating device.

44. The mist-generating device of claim 32, further comprising at least one baffle mounted in the misting chamber.

45. The mist-generating device of claim 32, further comprising an auto-shut-off system that is triggered by treatment time.

46. The mist generating device of claim 32, further comprising a low fluid level sensor.

47. The mist generating device of claim 32, further comprising a tilt-level sensor.

48. The mist-generating device of claim 32, further comprising a visual display to indicate a stage of treatment.

49. The mist-generating device of claim 32, further comprising a remote visual code display to indicate a stage of treatment.

50. The mist-generating device of claim 32, further comprising a readable visual code on a display that indicates a stage of treatment.

51. The mist-generating device of claim 32, further comprising a remote display that notifies an operator of a status of treatment.

52. The mist-generating device of claim 51, wherein the remote display is part of a wireless device.

53. The mist-generating device of claim 32, wherein the misting chamber defines a fluid inlet which is connected to a fluid reservoir, a check valve being mounted between the inlet and the fluid reservoir.

54. The mist-generating device of claim 13, further comprising a diagnostic port configured to be attached to a computer.

55. The mist-generating device of claim 13, further comprising a second memory device storing data associated with at least one of the following: (a) a number of cycles; (b) error codes; (c) a number of short cycles; (d) services; (e) time; (f) input voltage; (g) piezo current; (h) piezo voltage; (i) ambient temperature; (j) heat sink temperature; (k) machine code; and (l) operating status.

56. The mist-generating device of claim 13, wherein the at least one ultrasonic transducer is configured to operate with the processor, the inlet and the outlet to atomize between 2 and 20 milliliters of the designated fluid per minute.

57. A mist-generating device comprising:

a housing defining a misting chamber;

at least one ultrasonic transducer configured to atomize a designated fluid, and electrically connected to a power supply;

a memory device storing a plurality instructions which, when executed by a processor, cause the processor to operate with the power supply to monitor at least one of a voltage and a current to the at least one ultrasonic transducer;

an inlet to the misting chamber;

an outlet from the misting chamber in fluid connection with the at least one ultrasonic transducer;

a first anti-foam guard connected to a base of the housing configured to be in contact with the designated fluid and configured to reduce foaming and splashing of the designated fluid covering the at least one ultrasonic transducer; and a second anti-foam guard connected to top of the housing, wherein the at least one ultrasonic transducer is configured to operate with the processor, the inlet, and the outlet to atomize a programmed amount of the designated fluid per minute, and wherein an edge of the second anti-foam is aligned with and contacts an edge of the first anti-foam guard.

58. The mist-generating device of claim 57, further comprising:

a trap mechanism including a volume receptacle located at a base of the trap mechanism configured to cause the trap mechanism to pivot to the open position when an undesirable solution accumulates in the volume receptacle, wherein the trap mechanism includes an opening at a bottom of the volume receptacle that is configured to drain the undesirable solution accumulating within the volume receptacle.

* * * * *